US007785875B2

(12) United States Patent
Hwang et al.

(10) Patent No.: US 7,785,875 B2
(45) Date of Patent: Aug. 31, 2010

(54) POLYNUCLEOTIDE ENCODING HCV EPITOPES WHICH CAN BIND TO VARIOUS HLA SUPERTYPES, IMMUNOGENIC COMPOSITION COMPRISING SAME AND METHOD OF INDUCING AN HCV-SPECIFIC IMMUNE RESPONSE USING SAME

(75) Inventors: Yu Kyeong Hwang, Yongin-si (KR); Okjae Lim, Yongin-si (KR); Hyejin Chung, Yongin-si (KR)

(73) Assignee: Mogam Biotechnology Research Institute, Yongin-si (KR)

( * ) Notice: Subject to any disclaimer, the term of this patent is extended or adjusted under 35 U.S.C. 154(b) by 0 days.

(21) Appl. No.: 12/289,766

(22) Filed: Nov. 3, 2008

(65) Prior Publication Data

US 2009/0162317 A1 Jun. 25, 2009

Related U.S. Application Data

(63) Continuation-in-part of application No. 11/571,598, filed as application No. PCT/KR2005/002111 on Jul. 4, 2004, now abandoned.

(30) Foreign Application Priority Data

Jul. 3, 2004 (KR) .................... 10-2004-0051782

(51) Int. Cl.
 *C12N 15/00* (2006.01)
 *C07H 21/00* (2006.01)
 *A61K 31/7088* (2006.01)
 *A61K 39/00* (2006.01)
(52) U.S. Cl. .................... 435/320.1; 514/44; 536/23.72; 424/185.1; 424/192.1; 424/201.1; 424/228.1
(58) Field of Classification Search .................... None
See application file for complete search history.

(56) References Cited

U.S. PATENT DOCUMENTS

| | | | |
|---|---|---|---|
| 6,235,888 B1 | 5/2001 | Pachuk | |
| 6,297,048 B1 | 10/2001 | Jolly | |
| 6,392,028 B1 | 5/2002 | Rice et al. | |
| 6,562,346 B1 | 5/2003 | Paliard | |
| 6,607,727 B1 | 8/2003 | Chisari | |
| 6,685,944 B1 | 2/2004 | Berzofsky | |
| 6,689,368 B1 | 2/2004 | Leroux-Roels | |
| 7,022,830 B2* | 4/2006 | Sallberg | 536/23.72 |
| 2002/0192640 A1* | 12/2002 | Thibeault et al. | 435/5 |
| 2003/0206919 A1* | 11/2003 | Sallberg | 424/189.1 |
| 2004/0082531 A1* | 4/2004 | Catchpole et al. | 514/44 |

FOREIGN PATENT DOCUMENTS

| | | | |
|---|---|---|---|
| WO | 9420127 A1 | 9/1994 | |
| WO | 0034494 A1 | 6/2000 | |
| WO | 0174382 A1 | 10/2001 | |
| WO | 03090687 A2 | 11/2003 | |
| WO | 2005/042698 | 12/2005 | |

OTHER PUBLICATIONS

GenPept AAF65944, "polyprotein [Hepatitis C virus].," Apr. 2000.*
Grakoui et al., "A second hepatitis C virus-encoded proteinase," Proceedings of the National Academy of Sciences, USA, vol. 90, pp. 10583-10587 (Nov. 1993).*
Tabatabai et al., "Functionally distinct T-Cell epitopes within the hepatitis C virus non-structural 3 protein," Human Immunology, vol. 60 No. 2, pp. 105-115 (Feb. 1999).*
Wertheimer et al., "Novel CD4+ and CD8+ T-cell determinants within the NS3 protein in subjects with spontaneously resolved HCV infection," Hepatology, vol. 37 No. 3, pp. 577-589 (Mar. 2003).*
Ke JS, et al. "Enhancement of cellular immune response to DNA vaccine encoding hepatitis C virus core and envelope 2 fusion antigen by murine Fms-like tyrosine kinase 3 ligand", Sheng Wu Gong Cheng Xue Bao., vol. 19(2): 158-162, Mar. 2003.
Jong, J. Kim, et al. "Engineering DNA vaccines via co-delivery of co-stimulatory molecule genes", Vaccines, vol. 16(19): 1828-1835, (1998).
Ken-Ya Murata, et al. "Expression of the co-stinulatory molecule BB1, the ligands CTLA-4 and CD28 and their mRNAs in chronic inflammatory demyelinating polyneuropathy", Brain, vol. 123: 1660-1666, (2000).
Thimme, R., et al, "Degenerate Immunogenicity of an HLA-A2-Restricted Hepatitis B Virus Nucleocapsid Cytotoxic T-Lymphocyte Epitope That Is Also Presented by HLA-B51," J. of Virology, vol. 75, No. 8, Apr. 2001, p. 3984-3987.
Parker, K. C., et al., "Scheme for Ranking Potential HLA-A2 Binding Peptides Based on Independent Binding of Individual Peptide Side-Chains," J. of Immunology, 1994, pp. 163-175.
Reynolds, S.R., et al., "Identification of HLA-A*03, A*11, and B*07-restricted melanoma-associated peptides that are immunogenic in vivo by vaccine-induced immune response (VIIR) analysis," J. of Immunological Methods, 244 (2000) 59-67.
Sette, A., et al., "Nine major HLA class I supertypes account for the vast preponderance of HLA-A and —B polymorphism," Immunogenetics (1999) 50:201-212.
Sette, A., et al., "HLA supertypes and supermotifs: a functional perspective on HLA polymorphism," Immunology 1998; 10:478-482.
Urbani, S., et al., "Identification of Immunodominant Hepatitis C Virus (HCV)-Specific Cytotoxic T-cell Epitopes by Stimulation with Endogenously Synthesized HCV Antigens," Hepatology, Jun. 2001, pp. 1533-1543.
Heile et al.; "Evaluation of hepatitis C virus glycoprotein E2 for vaccine design; an endoplasmic reticulum-retained recombinanat protein is superior to secreted recombinant protein and DNA-based vaccine candidates," Journal of Virology, vol. 74 No. 15, pp. 6885-6892 (Aug. 2000).
GenBank AB049089, "Hepatitis C virus gene for polyprotein, complete cds, isolate: HCVT109," Dec. 2000.
Koziel et al., "Heptatits C virus (HCV)-specific cytotoxic T lymphocytes recognize epitopes in the core and envelope proteins of HCV," Journal of Virology, vol. 67 No. 12, pp. 7522-7532 (Dec. 1993).

(Continued)

*Primary Examiner*—Zachariah Lucas
(74) *Attorney, Agent, or Firm*—Sughrue Mion, PLLC

(57) ABSTRACT

There are provided a polynucleotide encoding HCV epitopes, an immunogenic composition including same, and a method of inducing an HCV-specific immune response using same.

15 Claims, 11 Drawing Sheets

OTHER PUBLICATIONS

Manns et al, "The way forward in HCV treatment—finding the right path," Nature Review Drug Discovery, vol. 6 No. 12 pp. 991-1000 (Dec. 2007).

Rollier et al., "Control of Heterologous Hepterologous Hepatitis C Virus Infection in Chimpanzees Is Associated with the Quality of Vaccine-Induced Peripheral T-Helper Immune Response," Journal of Virology, vol. 78 No. 1, pp. 187-196 (Jan. 2004).

Sarobe et al.; "Characterization of an immunologically conserved epitope from hepatitis C virus E2 glycoprotein recognized by HLA-A2 restricted cytotoxic T lymphocytes," Journal of Hepatology, vol. 34 No. 2, pp. 321-329 (Feb. 2001).

Shirai et al., "An epitope in hepatitis C virus core region recognized by cytotoxoc T cells in mice and humans," Journal of Virology, vol. 68 No. 5, pp. 3334-3342 (May 1994).

Chang, K-M., et al., "Identification of HLA-A3 and -B7-Restricted CTL Response to Hepatitis C Virus in Patients with Acute and Chronic Hepatitis C[1]," J. of Immunology, 1999, pp. 1156-1164.

Wilson, C.C., et al., "Development of DNA Vaccine Designed to Induce Cytotoxic T Lymphocyte Responses to Multiple Conserved Epitopes in HIV-1[1]," J. of Immunology, 2003, pp. 5611-5623.

Jens Encke et al., General Session 2: Basic Virology, Journal of Hepatology, Apr. 1, 2002, p. 5, vol. 36, Supplement 1.

Noriyoshi Kuzushita et al., The Use of NS5 Protein-Transduced Dendritic Cells As a Novel Approach For Vaccination Against Hepatitis C Virus, Hepatology, 2003, p. 185A, vol. 38, Suppl. 1.

Ke Jin-Shan et al., Enhancement of Cellular Immune Response to DNA Vaccine Encoding Hepatitis C Virus Core and Envelope 2 Fusion Antigen by Murine Fms-Like Tyrosine Kinase 3 Ligand, Mar. 2003, pp. 158-162, vol. 19, No. 2.

Sanjay Gurunathan et al., CD40 Ligand/Trimer DNA Enhances Both Humoral and Cellular Immune Responses and Induces Protective Immunity to Infectious and Tumor Challenge, 1998, pp. 4563-4571, 161.

* cited by examiner (A)

(B)

POLYNUCLEOTIDE ENCODING HCV EPITOPES WHICH CAN BIND TO VARIOUS HLA SUPERTYPES, IMMUNOGENIC COMPOSITION COMPRISING SAME AND METHOD OF INDUCING AN HCV-SPECIFIC IMMUNE RESPONSE USING SAME

CROSS REFERENCE TO RELATED APPLICATION

This application is a continuation-in-part application of U.S. application Ser. No. 11/571,598 filed on Jan. 3, 2007 (now abandoned), which is a national stage application under 35 U.S.C. §371 of PCT/KR2005/002111 filed on Jul. 4, 2004, which claim priority from Korean patent application 10-2004-0051782 filed on Jul. 3, 2004, the disclosures of which are incorporated herein by reference.

FIELD OF THE INVENTION

The present invention relates to HCV epitopes and use thereof, and more particularly, to a polynucleotide encoding HCV epitopes which can bind to various HLA supertypes, an immunogenic composition comprising same, and a method of inducing a HCV-specific immune response using same.

BACKGROUND OF THE INVENTION

Hepatitis C virus (HCV) is a major cause of chronic liver diseases, hepatic cirrhosis and hepatocellular carcinoma. More than half of HCV-infected patients develop chronic hepatitis which leads to lethal cirrhosis or hepatoma. It is reported that approximately 170 million people, more than 3% of total earth population, are infected with HCV (Miller and Purcell, *Proc. Natl. Acad. Sci. USA,* 87: 2057-2061 (2000)). The conventional treatment method for HCV-infected patients involves the administration of interferon (α-interferon) or ribavirin. However, just about 50% of these patients respond to interferon, and 50% of the treated patients suffer from relapsed hepatitis C (Hino et al., *J. Med. Virol.* 42(3):299-305 (1994); Tsubota et al., *Hepatology.* 19(5):1088-94 (1994)). Another problem of interferon-based treatment is the high cost of the treatment which requires hospitalization. Although ribavirin, one of nucleic acid derivatives, works effectively for 40 to 70% of acute hepatitis patients, it is not effective for chronically HCV-infected patients.

Any successful treatment or preventive method for HCV infection or HCV-mediated chronic liver disease has not yet been developed. Therefore, there remains a need to develop a HCV-specific antiviral agent.

HCV belongs to Flaviviridae family causing non-A non-B hepatitis. HCV genome comprises a single-stranded RNA which expresses a polyprotein composed of 3,010 amino acids (Choo et al., *Science,* 244:359-362 (1989)). The HCV polyprotein is cut by virus or host cell proteases into 10 functionally different proteins. HCV is composed of a row of genes, namely NH2-C-E1-E2-p7-NS2-NS3-NS4A-NS4B-NS5A-NS5B-COOH (Steven Rosenberg, *J. Mol. Biol.,* 313: 451-464 (2001)), which are classified into two groups: one, structural proteins including C (core), E1, E2 and p7 and the other, non-structural proteins including NS2, NS3, NS4A, NS4B, NS5A and NS5B.

C (core) protein of HCV is believed to be responsible for the encapsidation of HCV genomic RNA and to play an important role in the development of hepatoma by regulating gene transcription, growth and proliferation of host cells. E1 and E2 proteins are type-1 transmembrane and virus envelope proteins, known to be involved in cell infection. E1 protein had not been studied in detail in the past because of its incapability of inducing neutralizing antibody. Recently, however, a therapeutic vaccine using E1 has been developed by Innogenetics, Co. (Belgium), which is in the process of phase II clinical trial following successful phase I clinical trial with chimpanzees. It is encouraging that E1 protein can be effectively used for the treatment of 1b type HCV infection which has not been successfully treated by alpha-interferon. E2 protein, one of critical envelope proteins of HCV, has been known as a multi-functional protein which conjugates with the assumed cell receptor CD81, and it nullifies both the immune system's ability to action of a host cell and interferon-mediated antiviral reaction, which leads to oncogenesis or autoimmune liver disease. Thus, E2 is a major target for the development of an anti-HCV agent. The function of P7 protein has not yet been disclosed. NS2 protein is a part of a metallo-protease, and NS3 harbors serine protease of HCV at its N-terminus and RNA helicase domain of its C-terminus. NS4A is a cofactor of viral protease, and NS4B has been found by the present inventors to have a potential for tumorigenesis. NS5A functions to endow HCV resistance against interferon and antiapoptosis. NS5B acts as a viral RNA-dependent RNA polymerase. Non-structural proteins including NS2, NS3, NS4B and NS5B have also been the major targets for the development of antiviral agent inhibiting viral replication.

Cytotoxic T lymphocytes (CTLs) play an important role in eradicating virus from a virus-infected individual. Once infected with HBV, a patient develops an acute hepatitis. However, in most acute hepatitis B patients, a powerful polyclonal CTL response occurs, leading to the natural cure of the disease, but a significant CTL response cannot be induced in chronic hepatitis B patients.

Even when HCV-specific CTL response is induced in the liver and peripheral blood of chronically HCV-infected patients, such CTL response is too weak to get rid of the virus effectively. Nevertheless, a number of research efforts have showed that HCV infection can be controlled by HCV-specific CTL response, suggesting that it is possible to develop an effective antiviral therapy based on the amplification of HCV-specific CTL response.

An epitope inducing antiviral CTL response can induce very effective cellular immunity for the prevention or treatment of viral infection. The use of an antigen-specific epitope or a DNA construct encoding the epitope is more advantageous than that of a conventional whole protein antigen. First, it is safe. Second, there is no likelihood of reducing an immune response due to mutation, unlike the case when a whole protein antigen is used. Third, it can be produced easily. Fourth, it is easy to produce a multi- or poly-vaccine using epitopes originating from multiple antigens of pathogens.

However, epitope-based vaccine and the treatment therewith has been limitedly applied due to the polymorphism of HLA (human leukocyte antigen) (hereinafter, also referred to as "MHC (major histocompatibility complex)") and the diversity of the epitopes binding to HLA subtypes. Up to now, most studies on antigen-specific antiviral CD8+ T cell response have been focused on HLA-A2 positive patients.

To induce a cellular immunity, an epitope peptide must be exposed on the surface of an antigen-presenting cell (APC) for forming a complex with MHC on APC. When T cell receptors (TCRs) on the surfaces of T cells recognize the structure of the MHC-peptide complex, the information on the recognized antigen is transferred to the T cells, which are activated by the interaction of CD40 with CD40L, the ligand of CD40 on the surfaces of APCs. Signal transduction through the CD40-CD40L interaction stimulates APCs, leading to the expression of co-stimulatory molecules such as B7-1 and B7-2. As a result, T cells can function as effector T cells having active molecules like CD28, 4-1BB, and CD25.

In chronic hepatitis patients, the expression of co-stimulatory molecules, which are known to promote a CTL-mediated immune response, is reduced and the maturation of dendritic cells known as APCs is inhibited, while the function and the number of natural killer cells become low. In this regard, it is expected that the administration of such a co-stimulatory molecule can enhance cellular immunity. Thus, the present inventors demonstrated that the cellular immunity can be enhanced by such a cofactor as: CD40LT, a trimer form of CD40L which induces the maturity of dendritic cells; 4-1BBL which increases the density of CD8+ T cells and promotes the functions of memory T cells; IL-15 and FLT-3L which induce the maturity of dendritic cells and promote the functions of natural killer cells that are depleted in HCV-infected patients; B7-1 and B7-2 which play important roles in recognizing epitope antigen; and HSP (Heat shock protein) which improves the epitope-presenting process.

The use of a peptide antigen is safer and more effective than the use of a whole protein antigen, but has some limitations in that the costs for peptide synthesis and purification are high and a specific antigen delivery system is required. An exogenous peptide antigen cannot be expected to match the entire processes of epitope generation from endogenous antigen like tumor antigen or viral antigen. The antigenicity is significantly affected by the physical properties of the peptide, while a DNA antigen has advantages over a peptide antigen such as: the production cost is low; the easiness of handling; and its effectiveness in process of epitope generation inside cells without any special means for the presentation and recognition of tumor or viral antigens. It is reported that a DNA antigen induces an effective cell-mediated immune when it is provided in the form of a eukaryotic expression vector (Cara C Wilson et al. *J. Immunol.*, 171:5611-5623 (2003)).

To overcome the above-mentioned limitations of the conventional epitope-based immunotherapy and to induce a strong HCV-specific CTL response, the present inventors have designed multi-HLA supertype reactive epitopes from the conservative regions of HCV polyprotein through motif search, and found that the epitopes induce an effective HCV-specific immune response by their binding to not only HLA-A2 type but also other HLA-A and HLA-B types. The present inventors have also found that when an expression vector including an epitope-encoding oligonucleotide or polynucleotide is administered to an animal model, an effective HCV-specific immune response can be induced.

SUMMARY OF THE INVENTION

Accordingly, the objects of the present invention are to provide HCV epitopes capable of effectively inducing an HCV-specific cytotoxic T lymphocyte (CTL)-mediated immune response to various HLA-A and HLA-B supertypes from patients, and a use thereof.

In accordance with an aspect of the present invention, there is provided a polynucleotide comprising nucleotide sequences as set forth in SEQ ID NOS: 1, 3, 5, 7, 9, 11, 13, 15, 17 and 19, each of which encodes an HCV epitope inducing an HCV-specific immune response by reacting with HLA-A and HLA-B supertype molecules.

In accordance with another aspect of the present invention, there is provided a eukaryotic expression vector comprising the polynucleotide.

In accordance with another aspect of the present invention, there is provided an immunogenic composition comprising the polynucleotide.

In accordance with a further aspect of the present invention, there is provided a method of inducing an HCV-specific immune response to HLA-A and HLA-B types, comprising administering the polynucleotide to a subject.

BRIEF DESCRIPTION OF THE DRAWINGS

The above and other objects and features of the present invention will become apparent from the following description of the invention, when taken in conjunction with the accompanying drawings, which respectively show.

Figure 1:
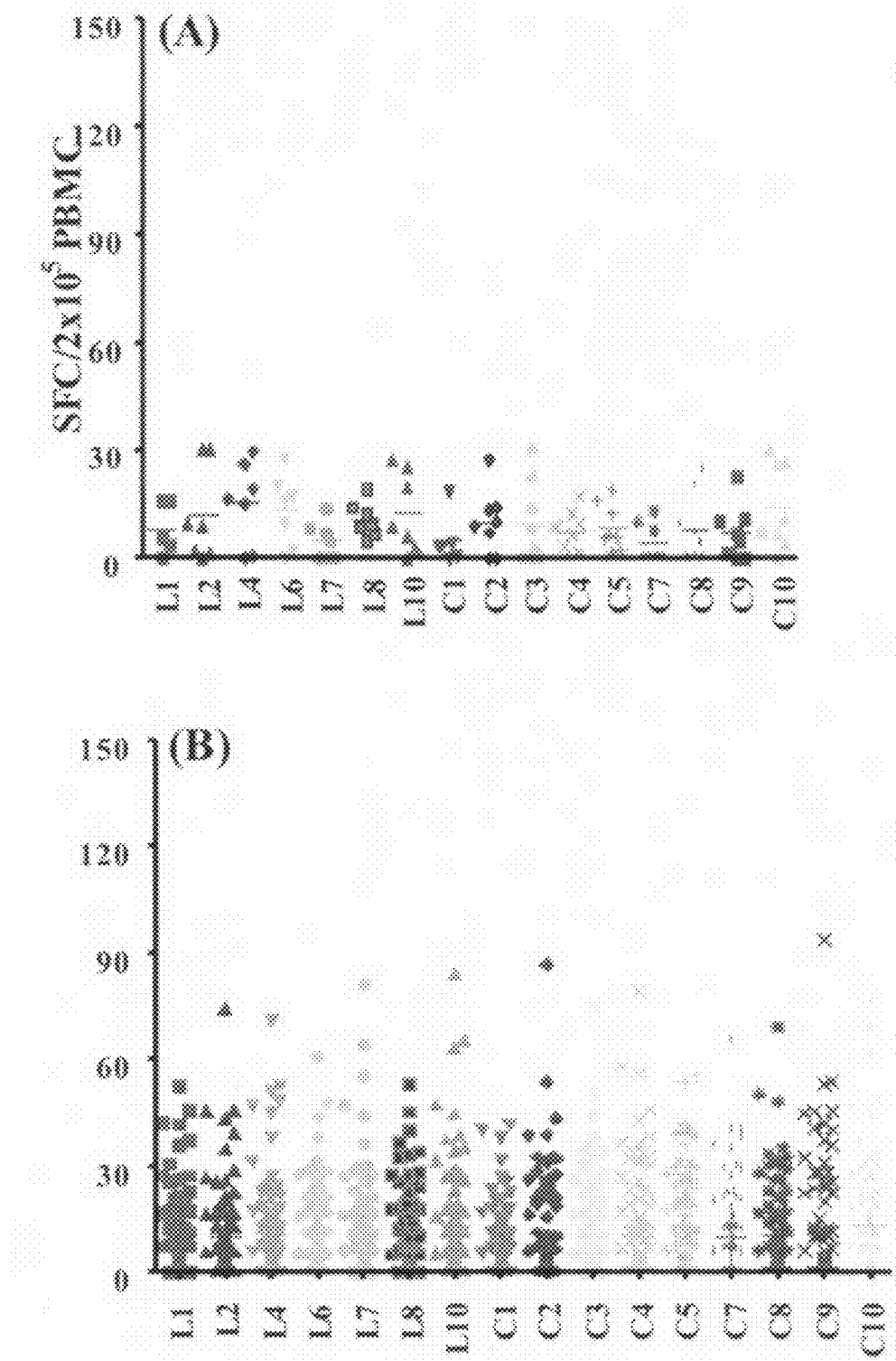
FIG. 1: a view illustrating the increased secretion level of cytokine IFN-γ in HCV-infected patients, which was determined by ex vivo ELISPOT assay after administering the epitopes of the present invention.
(A): Normal subject group
(B): HCV patients group

(A): memory T cell response to invented epitopes in Chimp 1

(B): memory T cell response to pre-existing epitopes in Chimp 3

DMSO: dimethyl sulfoxide (negative control)

PHA: phytohemagglutinin (positive control)

DETAILED DESCRIPTION OF THE INVENTION

Unless defined otherwise, technical and scientific terms used herein have the same meanings that are commonly used by those of ordinary skill in the art.

The term "epitope" used herein means a specific region that combines with an antibody, a T cell receptor (TCR) or a major histocompatibility complex (MHC). It is also called "antigenic determinant."

The term "peripheral blood mononuclear cells (PBMCs)" used herein means blood cells, each of which has one nucleus, for example lymphocytes and macrophages.

The term "ELISPOT (enzyme-linked immunosorbent spot)" used herein means an immunoassay based on ELISA (enzyme-linked immunosorbent assay), but it is different from ELISA in that ELISA is a method of quantifying a protein using an antibody against the protein, while ELISPOT is a method of measuring the number of cells secreting cytokine by culturing cells on a nitrocellulose well coated with a cytokine-specific antibody, staining cytokine on the bottom of the well and counting the number of stained spots. ELISPOT is mainly used for the measurement of the number of antigen-specific cytotoxic T cells activated in a spleen sample obtained from an immunized animal.

The term "dendritic cells" used herein means antigen-presenting cells having a characteristic dendritic morphology like nerve cells. Examples of dendritic cells include Langerhans cells found in skin and granular dendritic cells found in lymph nodes.

The term "antigen-presenting cells (APCs)" used herein means cells that provide a foreign antigen, and mediate the innate immunity and the adaptive immunity, wherein the antigen is provided by MHC of the APCs. Examples of APCs include macrophages, B cells, dendritic cells, and keratinocytes.

The term "fluorescent activated cell sorting (FACS)" used herein, which is also called flow cytometry, means a method of sorting fluorescent material-labeled cells in a fluid stream by measuring the fluorescence intensity, which enables the quantification of the cells emitting a specific fluorescent wavelength, to determine the exact ratio of the target cells to total cells.

The term "intracellular cytokine staining (ICS)" used herein means a method of analyzing the T-cell capacity for producing cytokine in response to a specific stimulus. The general cytokine secretion pathway is blocked and the accumulation of the cytokine in a cell is measured by intracellular staining and FACS analysis.

The term "proteasome" used herein means a protease complex capable of cutting a protein into short polypeptides and amino acids by ATP reaction.

The term "transporter associated with antigen processing (TAP)" used herein means a transmembrane protein which transfers the antigen peptide produced by the action of proteasome from cytosol into ER. The antigen peptide migrated to ER binds with MHC class I molecule.

The term "TAP tool" used herein means a tool for predicting the TAP related processing, and more precisely, a tool for predicting the result of a specific antigen process and the sequence of the epitope presented therefrom. The TAP tool is performed using a computer software based on algorithms for statistical analysis, which includes a TAP binding prediction tool, a proteasome related processing prediction tool, and a finishing prediction tool by amino-peptidase in ER prediction tool. In the present invention, the tool means a proteasome related processing prediction tool and a TAP binding prediction tool.

The term "immunologically effective amount (dosage)" used herein means an amount required to induce an HCV-specific CTL-mediated immune response, more precisely, an amount required to stamp out HCV infection in a patient or to prevent HCV infection in a susceptible individual.

Hereinafter, the present invention is described in detail.

The present invention provides HCV epitopes having amino acid sequences as set forth in SEQ ID NOS: 2, 4, 6, 8, 10, 12, 14, 16, 18, 20, 22, 24, 26, 28, 30 and 32, each of which induces an effective HCV-specific CTL-mediated immune response by interacting with various HLA-A and HLA-B types.

The present inventors isolated the epitopes from the conservative regions of HCV polyprotein through motif search to overcome the limitations of conventional epitope-based immunotherapy and to induce an effective HCV-specific CTL-mediated immune response. To develop a vaccine which can be utilized industrially and applied to a broad spectrum of patients, the use of epitopes that can bind to polymorphic HLA molecules is required.

The biggest obstacle in the development of an epitope-based immunotherapeutic agent is polymorphism of HLA molecules. Thus, a number of epitopes are required to develop an effective immunotherapeutic agent. If a single epitope can bind to a variety of HLA molecules, the effect of the epitope-based vaccine will be wider and greater. In view of this problem, while searching for a method of inducing a full immune response against HCV, the present inventors have found epitopes capable of binding to multiple HLA supertype molecules.

CTL recognizes a short peptide composed of 8-11 amino acids. The 16 epitopes of the present invention, each of which is composed of 9 amino acids, can fully amplify an anti-HCV immune response especially in the chronic hepatitis C patients.

The epitopes of the present invention are originated from the conservative regions of HCV polyprotein, and have a broad and moderate binding capacity to HLA-A molecules such as A1, A2, A24, A26 and A3, and to HLA-B molecules such as B7, B8, B15, B27, B44 and B51. Generally, dominant epitopes show immune tolerance in chronically HCV-infected patients, while minor or subdominant epitopes are still active. Although the inventive epitopes do not exhibit an especially high binding capacity to a specific HLA type, they can respond to various HLA types and induce an increased secretion of interferon-γ (IFN-γ) from HCV-infected patients. This means that the inventive epitopes can escape immune tolerance against a dominant epitope, thereby resulting in the treatment of chronically HCV-infected patients like minor or subdominant epitopes.

That is, the inventive epitopes can effectively induce HCV-specific cellular immunity to various HLA-A and HLA-B molecules, which leads to the treatment of HCV-infected patients with different HLA types or the protection of persons with different HLA types from HCV infection.

In general, activated T-cells secret a number of cytokines, including IL-2, IL-4, IL-5, IL-10 and interferon-γ (IFN-γ), in response to a stimulus such as an antigen. Such a CTL response has been mainly determined by ELISPOT assay with good sensitivity and specificity, which is one of methods widely used to analyze the secretion of cytokines in a single cell. Thus, the present inventors have demonstrated an effective CTL-mediated immune response of the inventive epitopes by ELISPOT assay.

It is generally interpreted that an epitope-induced HCV-specific CTL response means the activation of CTLs against HCV. In ELISPOT assay, the degree of activation of CTLs against HCV is generally determined by subtracting the secretion level of cytokine in an epitope-untreated control group from that of an epitope-treated test group. However, this method might not be accurate since the data value of the control group may be changed according to an individual. Thus, in the present invention, to evaluate an epitope-induced CTL-mediated immune response more accurately, the degree of CTL activation was determined by subtracting the data value in the absence of an epitope from that in the presence of an epitope in a person, and the degree of the activation in HCV patients was compared to that of normal persons (Heiner Wedemeyer et al., *J. Immunol.* 169; 3447-3458 (2002)). The cutting value for positive reaction was determined by calculating the average data value of the control group and doubling the average value considering a standard deviation.

The epitopes of the present invention, when combined with a DNA vaccine, a therapeutic protein, a recombinant virus vaccine or dendritic cells, can induce an immune response more efficiently, thereby leading to more efficient treatment or prevention of HCV infection or HCV-mediated liver diseases.

The epitopes of the present invention can be used as a homopolymer containing multiple copies or a heteropolymer containing different peptides. The use of such a polymer is cost-effective and induces a significantly increased CTL response against an antigen determinant of pathogenic organism or the like.

In this regard, while searching for preferable combination of the inventive epitopes, the present inventors have found that the 10 epitopes having the amino acid sequences as set forth in SEQ ID NOS: 2, 4, 6, 8, 10, 12, 14, 16, 18 and 20 exhibit a significantly increased secretion of IFN-γ, and a polypeptide comprising the 10 epitopes can induce an effective HCV-specific immune response by the reaction of the respective epitopes in patients with various HLA-A and HLA-B types.

Thus, the present invention provides a polypeptide comprising the amino acid sequences as set forth in SEQ ID NOS: 2, 4, 6, 8, 10, 12, 14, 16, 18 and 20.

The polypeptide may further comprise at least one selected from the group consisting of amino acid sequences as set forth in SEQ ID NOS: 22, 24, 26, 28, 30 and 32.

The present invention also provides an immunogenic composition comprising at least one selected from the group consisting of the HCV epitopes having the amino acid sequences as set forth in SEQ ID NOS: 2, 4, 6, 8, 10, 12, 14, 16, 18, 20, 22, 24, 26, 28, 30 and 32.

Preferably, the immunogenic composition may comprise a polypeptide comprising the amino acid sequences as set forth in SEQ ID NOS: 2, 4, 6, 8, 10, 12, 14, 16, 18 and 20. In this case, the polypeptide may further comprise at least one selected from the group consisting of the amino acid sequences as set forth in SEQ ID NOS: 22, 24, 26, 28, 30 and 32.

The immunogenic composition of the present invention may further comprise an immune-stimulating factor (cofactor). Examples of the cofactor include, but are not limited to, CD40LT, a trimer form of CD40L that accelerates the maturity of dendritic cells; 4-1 BBL known to increase the number of CD8+ T cells and particularly to enhance the function of memory T cells; IL-15 and FLT-3L that enhance the maturity of dendritic cells and the function of natural killer cells deficient in HCV patients; B7-1 and B7-2 that play important roles in recognition of an epitope; and a heat shock protein (HSP) that enhances an epitope-presenting process.

Carriers commonly known in the art, for example thyroglobulin, human serum albumin, tetanus toxoid, or polyamino acid (e.g., poly-L-lysine, poly-L-glutamic acid) can also be included in the immunogenic composition of the present invention. The immunogenic composition may further comprise a physiologically acceptable diluent such as water or saline, preferably a phosphate buffered saline. The immunogenic composition may also comprise an adjuvant such as incomplete Freund's adjuvant, aluminum phosphate, aluminum hydroxide, or alum.

The inventive immunogenic composition may be administered to a host through various routes such as intradermal, epidermal, subcutaneous, intraperitoneal or intramuscular injection, oral inoculation, nasal inoculation, etc. Thus, the host can acquire HCV-specific cellular immunity, and thus, prevent the acute onset of HCV infection and the development of chronic infection.

The immunogenic composition of the present invention may further comprise dendritic cells (DC) as an epitope carrier. For example, antigen-loaded dendritic cells obtained by transfecting or pulsing dendritic cells with DNA encoding at least one of the inventive epitopes may be administered to a patient to induce an in vivo immune response.

The loading of the inventive epitopes on dendritic cells can also be achieved in vivo.

The immunogenic composition of the present invention can be used together with an immunoregulatory substance (e.g., IFN-γ) or other therapeutic agent(s) for chronic virus infection.

The present invention also provides a method of inducing an HCV-specific immune response to various HLA-A and HLA-B types, comprising administering to a subject at least one selected from the group consisting of the HCV epitopes having the amino acid sequences as set forth in SEQ ID NOS: 2, 4, 6, 8, 10, 12, 14, 16, 18, 20, 22, 24, 26, 28, 30 and 32.

Preferably, the HCV epitopes of SEQ ID NOS: 2, 4, 6, 8, 10, 12, 14, 16, 18 and 20 may be administered in the form of a single polypeptide to the subject.

Figure 4:
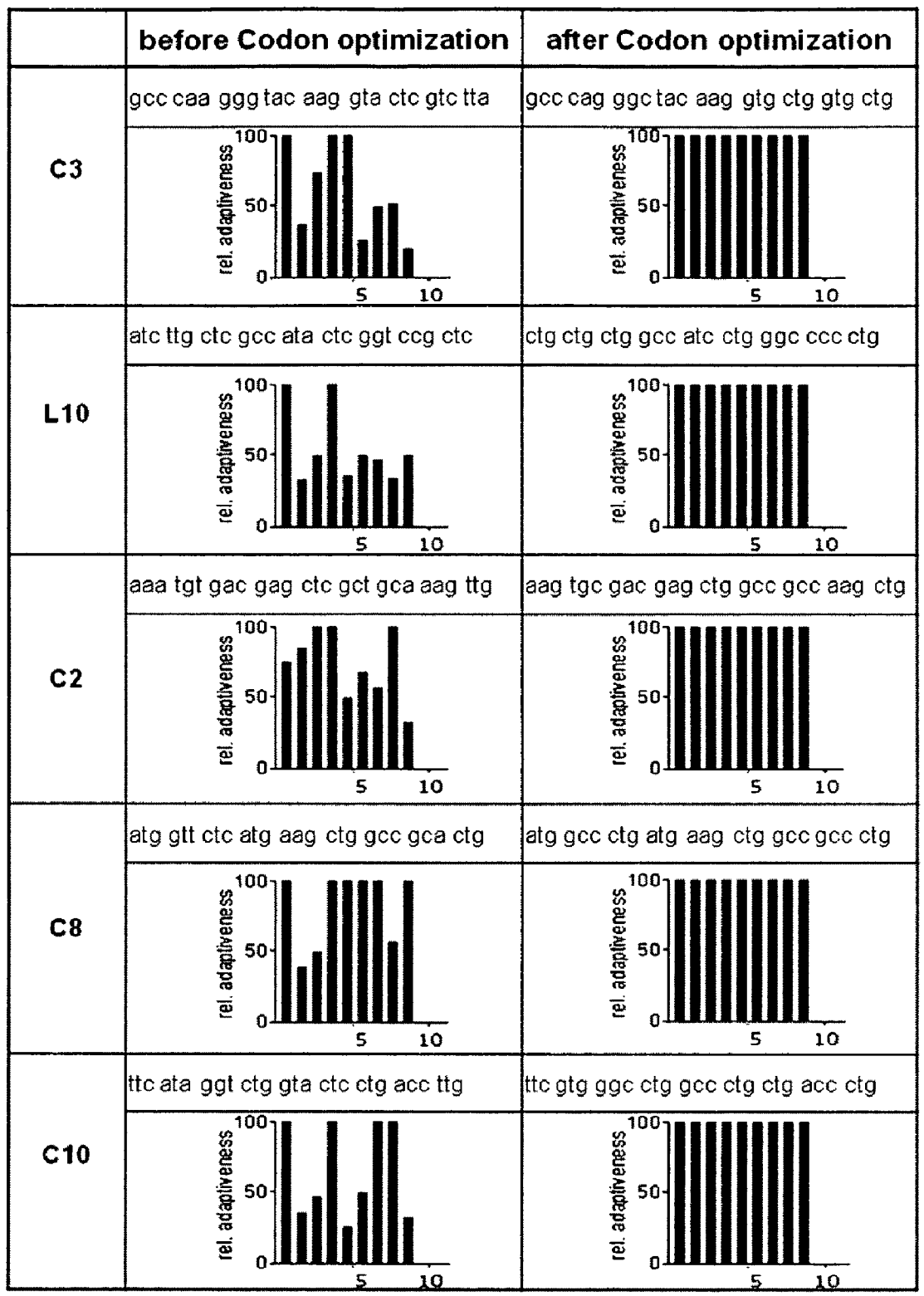
FIG. 4: the result of codon optimization for oligonucleotides having nucleotide sequences of SEQ ID NOS: 1, 3, 5, 7, 9, 11, 13, 15, 17 and 19.
Figure 4:
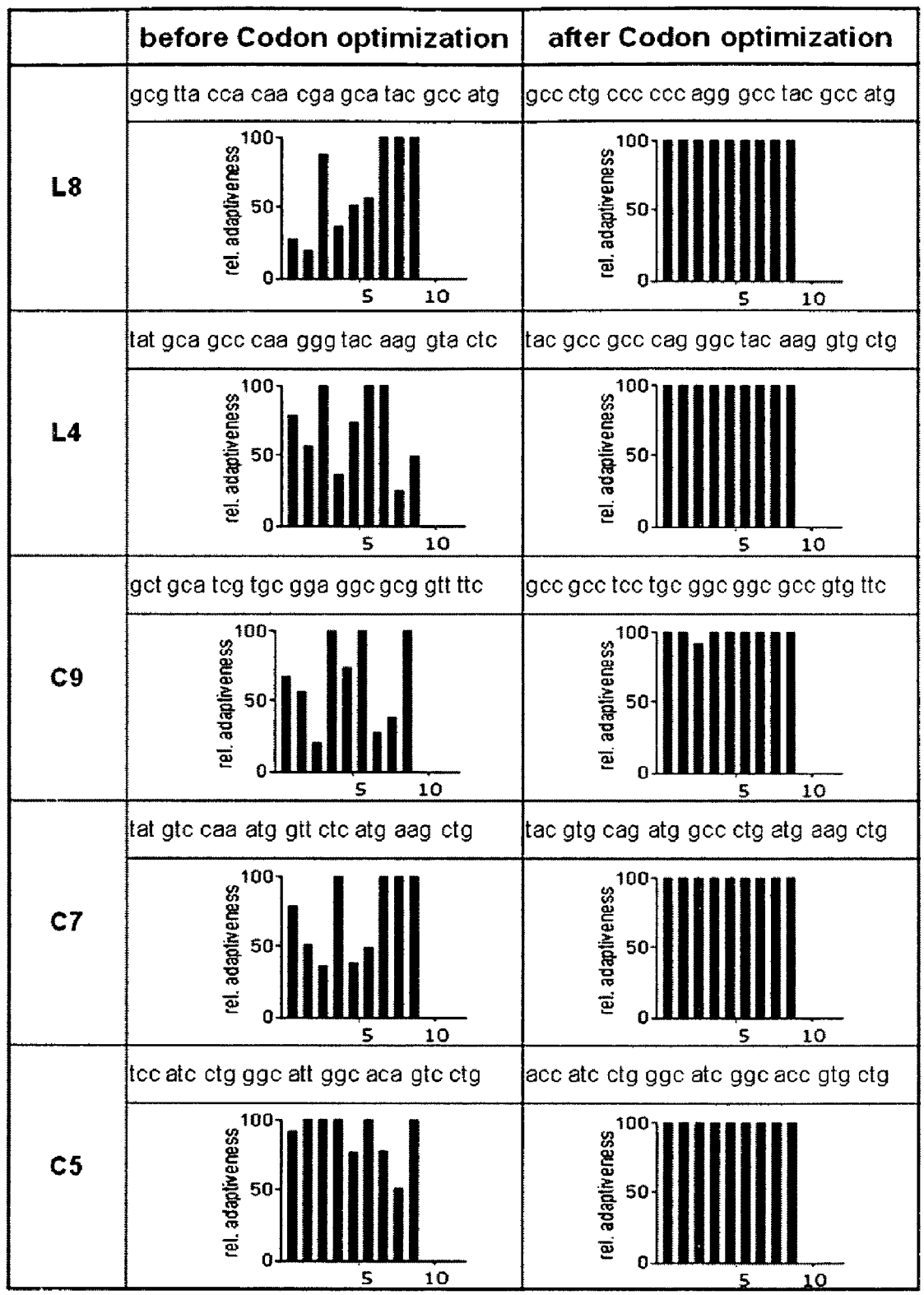

Meanwhile, the present inventors have identified the nucleotide sequences of the 16 epitopes isolated through motif search, and conducted codon optimization for the 10 epitopes, i.e., L4, L8, L10, C2, C3, C5, C7, C8, C9, and C10, to provide a higher degree of codon adaptiveness for efficient expression of them in mammalian cells. The results of the codon optimization are shown in FIG. 4.

Thus, the present invention provides oligonucleotides having nucleotide sequences as set forth in SEQ ID NOS: 1, 3, 5, 7, 9, 11, 13, 15, 17, 19, 21, 23, 25, 27, 29 and 31, each of which encodes an HCV epitope inducing an effective HCV-specific immune response by reacting with various HLA-A and HLA-B types.

Preferably, the present invention provides a polynucleotide comprising the nucleotide sequences as set forth in SEQ ID NOS: 1, 3, 5, 7, 9, 11, 13, 15, 17 and 19.

When epitopes are encoded by a single oligonucleotide or polynucleotide, a polypeptide synthesized in cells should be processed into respective epitopes. A polypeptide synthesized in cytoplasm is cut by protease complex called 'proteosome' into small peptides, each of which is composed of 8-11 amino acids. The small peptides are carried onto MHC of APCs to be exposed on the surfaces of APCs, and then function as epitopes. In order to synthesize one or more epitopes from an oligonucleotide or a polynucleotide in vivo, IgK signal sequence can be added to 5'-end of the oligonucleotide or polynucleotide to guarantee proper intracellular processing. Successful cutting can be predicted by the prediction programs provided by the following web sites:

NetChop: cbs.dtu.dk/services/NetChop/

ParProc: paproc2.de/paproc1/paproc1.html

FragPredict: mpiib-berlin.mpg.de/MAPPP/expertquery.html.

An immunogenic composition comprising an oligonucleotide or polynucleotide encoding the inventive epitope(s) can effectively induce an HCV-specific CTL-mediated immune response.

In the inventive immunogenic composition, an epitope-encoding oligonucleotide or polynucleotide can be provided in the form of a eukaryotic expression vector. For gene expression, a well-known eukaryotic expression vector such as pcDNA3.1 or pVAX1 (Invitrogen) is available, and as a promoter, a CMV promoter, a Pff-1alpha promoter or a SV40 promoter can be used. It is reported that an immune response can be successfully induced in an animal transfected with an expression vector including an epitope-encoding DNA (Cara C. Wilson et al., *J. Immunol.*, 171; 5611-5623, 2003).

The expression vector can further include a cofactor-encoding gene. Examples of the cofactor as mentioned above may be included. A cofactor-encoding gene and an epitope-encoding oligonucleotide or polynucleotide can be inserted into a single expression vector or respective different expression vectors.

The inventive immunogenic composition comprising a peptide or an epitope-encoding DNA can be administered to a patient in an immunologically effective dosage. For example, the composition can be administered once or more, and once daily dosage of the epitope may be 1 to 250 µg, more preferably 5 to 50 µg. When an expression vector containing an epitope-encoding DNA is administered, the effective dosage of the epitope-encoding DNA may be 100 ng to 100 µg, more preferably 1 to 50 µg The following Examples are intended to further illustrate the present invention without limiting its scope. .

Example 1

Selection of HCV-Specific Candidate Epitopes Against HLA-A and HLA-B Types

<1-1> Screening of Candidate Epitopes by Computer Algorithm

Based on the fact that CTL recognizes a short peptide composed of 8-11 amino acids, the present inventors isolated 16 epitopes each composed of 9 amino acids to promote an HCV-specific CTL-mediated immune response.

In detail, the conservative regions of HCV polyprotein were analyzed using SYFPEITHI algorithms (web site: syfpeithi.de) based on well-known peptide-MHC binding motif. As a result, 16 peptides having amino acid sequences as set forth in SEQ ID NOS: 2, 4, 6, 8, 10, 12, 14, 16, 18, 20, 22, 24, 26, 28, 30 and 32 were predicted to have a moderate binding capacity to 5 HLA-A molecules, i.e., A1, A2, A24, A26 and A3, and 6 HLA-B molecules, i.e., B7, B8, B15, B27, B44, and B51, and designated as L4, L8, L10, C2, C3, C5, C7, C8, C9, C10, L1, L2, L6, L7, C1 and C4, respectively. The amino acid sequences of these peptides were identical to the sequences of HCV 1a and 1b subtypes. These peptides were synthesized (Peptron, Korea) for the following experiments. The predicted binding scores for each peptide are listed in Table 1 below.

TABLE 1

| Peptide No. | HLA-A alleles | | | | | HLA-B alleles | | | | | | | SUM |
|---|---|---|---|---|---|---|---|---|---|---|---|---|---|
| | A*0201 | A1 | A*2402 | A*26 | A3 | B*0702 | B*08 | B*1510 | B*2705 | B*2709 | B*4402 | B*5101 | |
| L1 | 26 | 3 | 13 | 13 | 15 | 12 | 17 | 13 | 17 | 10 | 15 | 13 | 167 |
| L2 | 19 | 5 | 11 | 18 | 13 | 13 | 10 | 14 | 15 | 11 | 12 | 12 | 153 |
| L4 | 19 | 5 | 10 | 8 | 7 | 12 | 15 | 16 | 15 | 10 | 13 | 22 | 152 |
| L6 | 21 | 2 | 1 | 15 | 17 | 10 | 7 | 1 | 3 | 11 | 2 | 11 | 101 |
| L7 | 24 | 3 | 15 | 27 | 14 | 12 | 19 | 12 | 19 | 12 | 19 | 10 | 186 |
| L8 | 20 | 6 | 4 | 2 | 22 | 10 | 15 | 9 | 12 | 12 | 11 | 2 | 125 |
| L9 | 20 | 5 | 12 | 26 | 18 | 13 | 11 | 12 | 18 | 13 | 17 | 8 | 173 |
| L10 | 28 | 1 | 13 | 15 | 15 | 12 | 16 | 10 | 14 | 13 | 13 | 12 | 162 |
| C1 | 20 | 1 | 12 | 13 | 12 | 15 | 23 | 15 | 13 | 11 | 14 | 23 | 172 |
| C2 | 18 | 12 | 15 | 12 | 10 | 13 | 12 | 11 | 18 | 13 | 14 | 11 | 159 |
| C3 | 17 | 9 | 12 | 14 | 11 | 17 | 22 | 13 | 15 | 13 | 16 | 13 | 172 |
| C4 | 19 | 4 | 12 | 16 | 24 | 14 | 10 | 10 | 19 | 11 | 17 | 7 | 163 |
| C5 | 22 | 3 | 14 | 16 | 20 | 15 | 14 | 14 | 18 | 13 | 14 | 14 | 177 |
| C6 | 20 | nd | nd | 16 | 19 | 7 | 1 | 1 | 5 | 10 | 3 | 11 | 93 |
| C7 | 17 | 6 | 23 | 10 | 5 | 8 | 9 | 3 | 16 | 11 | 17 | 14 | 139 |
| C8 | 24 | nd | 13 | 14 | 7 | 12 | 25 | 11 | 15 | 12 | 14 | 21 | 168 |
| C9 | 10 | 5 | 10 | 9 | 19 | 13 | 10 | 10 | 15 | 9 | 15 | 13 | 138 |
| C10 | 22 | 7 | 10 | 24 | 18 | 13 | 12 | 11 | 14 | 11 | 14 | 11 | 167 |

As shown in Table 1, it was predicted that individual peptides exhibited high or intermediate binding capacity to various HLA-A and HLA-B molecules.

<1-2> Calculation of Binding Affinity of Candidate Epitopes to Individual HLA Molecules In the Example, the binding capacity between the candidate epitopes and HLA molecules was determined by La Jolla Institute.

In detail, the 10 epitope peptides screened in Example <1-1> were mixed with individual HLA proteins, and a peptide concentration for 50% binding to an HLA protein was measured. The tested epitopes and HLA molecules are listed in Table 2 and 3 below.

TABLE 2

| | | HLA binding capacity (IC50 nM) | | | | | | | | | | | |
|---|---|---|---|---|---|---|---|---|---|---|---|---|---|
| Peptide | Protein | A*010 | A*020 | A*0202 | A*0203 | A*0206 | A*030 | A*110 | A*230 | A*2402 | A*290 | A*680 | A*6802 |
| C2 | NS3 | | 894 | 2528 | | | 28552 | | 14207 | 36095 | | 38902 | |
| C3 | NS3 | | 4876 | 34426 | | 63039 | | | | | | | |
| C5 | NS3 | | 6518 | 5602 | | 17166 | 4789 | | 7442 | | | | |
| C7 | NS2 | 108.4 | 7041 | 13239 | 3363 | 2056 | | | 18768 | 27968 | | | 422 |
| C8 | NS2 | | 5712 | 8580 | 6407 | 211 | 11412 | | 41894 | | | | 9861 |
| C9 | NS2 | | 9949 | 21349 | 26739 | 8299 | | | 5701 | 24524 | | | |
| C10 | NS2 | 7867 | 281 | | 32644 | 15233 | | | | | | | 37082 |
| L4 | NS3 | | 12075 | | 10802 | 54729 | | | | | | | 17873 |
| L8 | E2 | | 1939 | 19778 | 30512 | 5819 | | | 4752 | 14432 | 3922 | | |
| L10 | NS2 | | 347 | 9462 | 257 | 685 | | 11168 | | 35297 | 47752 | | |

TABLE 3

| Peptide | Protein | HLA binding capacity (IC50 nM) | | | | | |
|---|---|---|---|---|---|---|---|
| | | B*0702 | B*2705 | B*3501 | B*5101 | B*5301 | B*5401 |
| C2 | NS3 | | | 69566 | | | |
| C3 | NS3 | | | | | | |
| C5 | NS3 | 48766 | | | | | |
| C7 | NS2 | 2033 | | | 17350 | | |
| C8 | NS2 | 53 | | 778 | 971 | 15026 | 13480 |
| C9 | NS2 | 843 | | 3880 | 4001 | 59440 | |
| C10 | NS2 | 53942 | | | 3517 | 38626 | 2369 |
| L4 | NS3 | 1125 | | 5760 | 6260 | 50546 | 18221 |
| L8 | E2 | 10040 | 58956 | 17831 | 3433 | | |
| L10 | NS2 | 1532 | | | 1320 | 18111 | 2086 |

Table 2 and 3 show that to the contrary our predictions, most of the peptides have poor binding capacity to specific HLA molecules.

Example 2

Isolation of PBMCs from HCV-Infected Patients

The bond between an epitope and a HLA molecule on the surfaces of antigen-presenting cells (APCs) is essential for T cell activation. To determine whether the 16 peptides synthesized in Example 1 can bind with various MHCs, experiments were performed with blood samples of 99 HCV-infected patients (Yonsei University Medical Center, Seoul, Korea). All of those patients were suffering from persistent HCV infection. Seroconversion containing an anti-HCV antibody of those patients was confirmed by an HCV ELISA test system (Koma, Anti-HCV ELISA Kit), and HCV RNA was detected by RT-PCR (Roche Diagnostic Systems, Amplicor HCV TEST). Blood samples obtained from eight normal persons who were not infected by HCV or HBV were used as a control group. Serum ALT (alanine aminotransferase) activity of blood samples of those patients was 6-fold higher than that of the normal persons, and patients who were expected to develop a chronic liver disease by another causative factor(s) were excluded. Class I HLA typing for all the test and control groups was carried out by SSP HLA DNA typing tray (One Lamda).

Peripheral blood mononuclear cells (PBMCs) were isolated from blood samples taken from the HCV-infected patients and the normal persons using a Ficoll-Histopaque density gradient method (Sigma, St. Louis, Mo.). After washing the isolated PBMCs three times with HBSS (Life technologies, Grand Island, N.Y.), the PBMCs were immediately used or stored in a liquid nitrogen tank containing 90% FCS (Life technologies) and 10% DMSO (Sigma).

Example 3

Assay for Responsiveness of the Candidate Epitopes to Various MHC Types of HCV-Infected Patients Ex Vivo <3-1> ELISPOT Assay for T Cell-Mediated Immune Response Against the Candidate Epitopes in PBMCs Derived from HCV-Infected Patients In general, activated T cells induce the secretion of various cytokines in response to a stimulus such as an antigen. Such a CTL response can be monitored by enzyme-linked immunosorbent spot (ELISPOT) assay, which is the most sensitive and specialized method for measuring the production of cytokine in a single cell. Thus, in the present invention, an epitope-specific CTL-mediated immune response was determined by ELISPOT assay measuring the secretion of cytokine, interferon γ (IFN-γ).

In detail, the PBMCs obtained in Example <2-1> were thawed and cultured at 37° C. overnight in a R-10 medium (RPMI 1640 medium containing 10% FCS, 2 mM L-glutamine, 50 U/ml penicillin and 50 µg/ml streptomycin). 5 µg/ml of recombinant human anti-IFN-γ antibody (BD pharmingen) was loaded in each well of a 96-well nitrocellulose plate (Millipore, USA) and treated with PBS (phosphate-buffered saline) at 4° C. overnight. The wells were washed with PBS and incubated in PBS containing 5% FCS at room temperature for two hours to block non-specific binding. The peptides of Example 1 were diluted with the R-10 medium to a final volume of 10 µg/ml, and 100 µl of each peptide solution was loaded in each well of a 96-well nitrocellulose plate (Millipore, USA). PBMCs were resuspended in the R-10 medium to a concentration of $2 \times 10^6$ cells/ml, and 100 µl of the PBMC solution was then loaded in each peptide-containing well. The wells were incubated at 37° C. for 24 hours and then washed with PBS containing 0.05% Tween 20. Then, 100 µl of human IFN-γ (BD Pharmingen)-specific biotin-conjugated monoclonal antibody was added to each well to a concentration of 3 µg/ml, and the wells were incubated at room temperature for two hours. The wells were washed with PBS-T (0.5% Tween20, Sigma), treated with streptavidin-peroxidase complex (Kirkegaard & Perry Laboratories) and incubated at room temperature for two hours. After the reaction was terminated, color development was induced using an AEC (3-amino-9-ethyl carbazole) substrate solution. When proper spots were observed, color development was terminated with distilled water. The wells were dried at room temperature, and the number of cells secreting IFN-γ was counted under a microscope. The wells were dried overnight and the number of spots was counted with ELISPOT reader (AID). The number of peptide-specific IFN-γ spots was determined by subtracting the number of IFN-γ spots in the absence of a peptide from the number of IFN-γ spots in the presence of the peptide in each of the test group and the normal control group. The measurement of the number of spots was repeated three times for each group.

As a result of the ELISOPT assay, an average number of spots showing a positive response in a normal person was 12. The present inventors defined a cutting value as 30, which was obtained by doubling the average value (12) considering a standard deviation. That is, in ELISPOT assay using $2 \times 10^5$ PBMCs, when SFCs (spot-producing cells) were 30 or more, response was considered to be positive.

As shown in FIG. 1, the HCV-infected patients exhibited positive response to the 16 epitopes (see (B) of FIG. 1), unlike in normal persons (see (A) of FIG. 1).

Among the 16 epitopes, 10 epitopes, i.e., L4, L8, L10, C2, C3, C5, C7, C8, C9, and C10 exhibited a significantly increased secretion of IFN-γ.

3-2> Analysis for Responsiveness of the Candidate Epitopes to Various MHC Types of HCV-Infected Patients In the Example, the responsiveness of invented individual epitopes to various HLA molecules was determined by ex vivo ELISPOT assay.

In ELISPOT assay, the degree of activation of CTLs against HCV is generally determined by subtracting the secretion level of cytokine in an epitope-untreated control group from that of an epitope-treated test group. However, this method might not be accurate since the data value of the control group may be changed according to an individual. Thus, in the present invention, to evaluate an epitope-induced CTL-mediated immune response more accurately, the degree of CTL activation was determined by subtracting the data value in the absence of an epitope from that in the presence of an epitope in a person, and the degree of the activation in HCV patients was compared to that of normal persons (Heiner Wedemeyer et al., *J. Immunol.* 169: 3447-3458 (2002)). The cutting value for positive reaction was determined by calculating the average data value of the control group and doubling the average value considering a standard deviation. The responsiveness of positive reaction is presented in Tables 4 and 5 below.

TABLE 4

| | HLA-A | | | | HLA-B | | | | Unit: % |
|---|---|---|---|---|---|---|---|---|---|
| | A2 | A24 | A26 | A3 | B7 | B15 | B27 | B44 | B51 |
| L1 | 11.5 | 8.3 | 0 | 10.0 | 11.7 | 0 | 0 | 33.3 | 10.0 |
| L2 | 15.3 | 12.5 | 0 | 13.3 | 5.8 | 22.2 | 25.0 | 11.1 | 20.0 |
| L4 | 15.3 | 16.6 | 0 | 10.0 | 23.5 | 0 | 0 | 22.2 | 30.0 |
| L6 | 15.3 | 8.3 | 0 | 10.0 | 11.7 | 11.1 | 0 | 11.1 | 30.0 |
| L7 | 19.2 | 12.5 | 0 | 10.0 | 17.6 | 22.2 | 25.0 | 11.1 | 20.0 |
| L8 | 26.9 | 20.8 | 100 | 10.0 | 17.6 | 11.1 | 25.0 | 22.2 | 20.0 |
| L10 | 34.6 | 20.8 | 0 | 16.6 | 23.5 | 11.1 | 0 | 11.1 | 20.0 |
| C1 | 11.5 | 4.18 | 0 | 10.0 | 11.7 | 0 | 0 | 22.2 | 20.0 |
| C2 | 26.9 | 33.3 | 0 | 23.3 | 17.6 | 44.4 | 0 | 22.2 | 30.0 |
| C3 | 23.0 | 25.0 | 0 | 33.3 | 29.4 | 55.5 | 0 | 22.2 | 40.0 |
| C4 | 26.3 | 29.1 | 0 | 23.5 | 29.1 | 44.4 | 0 | 22.2 | 50.0 |
| C5 | 23.0 | 29.1 | 0 | 36.6 | 29.4 | 33.3 | 0 | 44.4 | 60.0 |
| C7 | 15.3 | 16.6 | 0 | 13.3 | 17.6 | 11.1 | 0 | 11.1 | 40.0 |
| C8 | 30.7 | 29.1 | 0 | 23.3 | 35.2 | 22.2 | 25.0 | 22.2 | 50.0 |
| C9 | 34.6 | 29.1 | 0 | 33.3 | 23.5 | 33.3 | 25.0 | 22.2 | 70.0 |
| C10 | 42.3 | 25.0 | 0 | 33.3 | 23.5 | 33.3 | 25.0 | 11.1 | 60.0 |
| Average | 23.26 | 20.0 | 6.25 | 19.36 | 20.54 | 22.2 | 9.37 | 20.1 | 35.6 |

TABLE 5

Number of patients showing positive response/Number of patients having specific MHC type

| | | | | HLA-A molecule | | | | | HLA-B molecule | | | | | |
|---|---|---|---|---|---|---|---|---|---|---|---|---|---|---|
| I.D. | SEQ ID NO: | HCV protein | Region | A2 | A1 | A24 | A26 | A3 | B7 | B8 | B15 | B27 | B44 | B51 |
| L1 | 22 | Core | 118 | 3/26 | | 2/24 | 0/1 | 3/30 | 2/17 | | 0/9 | 0/4 | 3/9 | 1/10 |
| L2 | 24 | E2 | 632 | 4/26 | | 3/24 | 0/1 | 4/30 | 1/17 | | 2/9 | 1/4 | 1/9 | 2/10 |
| L4 | 2 | NS3 | 1244 | 4/26 | | 4/24 | 0/1 | 3/30 | 4/17 | | 0/9 | 0/4 | 2/9 | 3/10 |
| L6 | 26 | E2 | 628 | 4/26 | | 2/24 | 0/1 | 3/30 | 2/17 | | 1/9 | 0/4 | 1/9 | 3/10 |
| L7 | 28 | NS2 | 883 | 5/26 | | 3/24 | 0/1 | 3/30 | 3/17 | | 2/9 | 1/4 | 1/9 | 2/10 |
| L8 | 4 | E2 | 802 | 7/26 | | 5/24 | 1/1 | 3/30 | 3/17 | | 1/9 | 1/4 | 2/9 | 2/10 |
| L10 | 6 | NS2 | 891 | 9/26 | | 5/24 | 0/1 | 5/30 | 4/17 | | 1/9 | 0/4 | 1/9 | 2/10 |
| C1 | 30 | NS3 | 1338 | 3/26 | | 1/24 | 0/1 | 3/30 | 2/17 | | 0/9 | 0/4 | 2/9 | 2/10 |
| C2 | 8 | NS3 | 1399 | 7/26 | | 8/24 | 0/1 | 7/30 | 3/17 | | 4/9 | 0/4 | 2/9 | 3/10 |
| C3 | 10 | NS3 | 1246 | 6/26 | | 6/24 | 0/1 | 10/30 | 5/17 | | 5/9 | 0/4 | 2/9 | 4/10 |
| C4 | 32 | NS2 | 894 | 7/26 | | 7/24 | 0/1 | 7/30 | 5/17 | | 4/9 | 0/4 | 2/9 | 5/10 |
| C5 | 12 | NS3 | 1325 | 6/26 | | 7/24 | 0/1 | 11/30 | 5/17 | | 3/9 | 0/4 | 4/9 | 6/10 |
| C7 | 14 | NS2 | 933 | 4/26 | | 4/24 | 0/1 | 4/30 | 3/17 | | 1/9 | 0/4 | 1/9 | 4/10 |
| C8 | 16 | NS2 | 936 | 8/26 | | 7/24 | 0/1 | 7/30 | 6/17 | | 2/9 | 1/4 | 2/9 | 5/10 |
| C9 | 18 | NS2 | 815 | 9/26 | | 7/24 | 0/1 | 10/30 | 4/17 | | 3/9 | 1/4 | 2/9 | 7/10 |
| C10 | 20 | NS2 | 823 | 11/26 | | 6/24 | 0/1 | 10/30 | 4/17 | | 3/9 | 1/4 | 1/9 | 6/10 |

As presented in Tables 4 and 5, the 16 peptides of Example 1 showed a great responsiveness to the patients who have 4 HLA-A phenotypes, i.e., A2, A24, A26, and A3, and 5 HLA-B phenotypes, i.e., B7, B15, B27, B44, and B51. That is, 23.26% of HLA-A2 type patients, 20.0% of HLA-A24 type patients, 6.25% of HLA-A26 type patients, and 19.36% of HLA-A3 type patients showed a positive response. In case of HLA-B type patients, 20.54% of HLA-B7 type patients, 22.2% of HLA-B15 type patients, 9.37% of HLA-B27 type patients, 20.1% of HLA-B44 type patients, and 35.6% of B51 type patients showed a positive response.

In more detail, L1 was positive to 6 HLA types; L2 was positive to 8 HLAs; L4 was positive to 6 HLAs; L6 was positive to 7 HLAs; L7 was positive to 8 HLAs; L8 was positive to 8 HLAs; L10 was positive to 7 HLAs; C1 was positive to 6 HLAs; C2 was positive to 7 HLAs; C3 was positive to 7 HLAs; C4 was positive to 7 HLAs; C5 was positive to 7 HLAs; C7 was positive to 7 HLAs; C8 was positive to 8 HLAs; C9 was positive to 8 HLAs; and C10 was positive to 8 HLA types.

Although neither A1 nor B8 types were found in the blood samples of 99 patients, considering the fact that a patient has at least 2-4 different HLA types, it is expected that the reaction frequency of an epitope to various HLA types in vivo is much greater than that of an epitope reacting to only a specific MHC type.

The above results show that the candidate epitopes can activate CTL responses from the patients with various MHC types.

Generally, a dominant epitope has a relatively high response to a specific HLA molecule with low responsiveness in chronic patients, while subdominant or minor epitopes have low binding affinity to a specific HLA molecule but have good responsiveness in the patients. Thus, the invented candidate epitopes are expected to be useful for the treatment of chronically HCV-infected patients with immune tolerance to a dominant epitope.

Example 4

ICS Analysis of Memory T Cell-Mediated Immune Response Against the Inventive Epitopes in PBMCs Derived from HCV-Infected Patients It is generally difficult to measure the activity of active T cells in blood of patients with chronic viral diseases. Thus, it is very meaningful to determine if an epitope can induce memory T cell-mediated immune response in patient's blood.

First, the PBMCs obtained in Example 2 were thawed and resuspended in a R-10 medium (RPMI 1640 medium containing 10% FCS, 0.2 mM L-glutamine, 50 U/ml penicillin and 50 μg/ml streptomycin) at 37° C. The cells were loaded into each well of a 96-well plate (Millipore) to a concentration of 5×10⁵ cells/100 μl.

The 10 epitopes selected in Example 3 were diluted with the R-10 medium to a final concentration of 20 μg/ml, and 100 μl of the epitope solution was then loaded into each well. Then, 10 ng/ml of recombinant IL-15 (recombinant human IL-15, R&D) was added to each well.

The wells were incubated at 37° C. for 5 days and treated with a secretion inhibitor (Golgi-Stop, BD Pharmingen) for 6 hours to arrest IFN-γ in cells. Then, 20 μg/ml of the inventive epitopes were added thereto and the cells were further cultured at 37° C. for 6 hours.

The cells were collected and incubated at 4° C. for 30 minutes in a 100-fold dilute solution obtained by diluting a human CD8 specific and FITC (Fluorescence Isothiocyanate) conjugated antibody with PBS containing 1% FBS (Gibco). Then, the cells were washed with PBS containing 1% FBS (Gibco) and fixed with formaldehyde-containing Cytofix/Cytoperm (BD Pharmingen) at 4° C. for 30 minutes. The cells were washed twice with a washing buffer (Perm/Wash buffer, BD Pharmingen). Then, 100 μl of a 200-fold dilute solution obtained by diluting a human IFN-γ (BD Pharmingen) specific and R-PE (R-pycoerythrin) conjugated monoclonal antibody with a Perm/Wash buffer (BD Pharmingen) was added to the cells, and the cell solution was incubated at 4° C. for 30 minutes. Then, the cells were further washed with the Perm/Wash buffer.

30,000 cells were acquired using FACS caliber (Becton Dnckinson) and analyzed with CellQuest software (Becton Dnckinson).

As a control group, memory T cell response was evaluated using normal person's blood and preexisting epitope peptides, i.e., C41, C36, C110, C132, NS4-1788, NS4-2510, and NS4-2588, as shown in Table 6 below.

TABLE 6

| MHC type | Peptide | Position | Protein | SEQ ID NO: |
|---|---|---|---|---|
| A2 | C36 | 36-44 | Core | 59 |
| | C132 | 132-140 | Core | 60 |
| | NS4-1789 | 1789-1797 | NS4 | 61 |
| A2 | NS5B-2510 | 2510-1518 | NS5B | 62 |
| | NS5B-2588 | 2588-2596 | NS5B | 63 |
| B7 | C41 | 41-49 | Core | 64 |
| | C110 | 110-118 | Core | 65 |

As a result of the ICS assay, among CD8+ cells of a normal control group, cells secreting IFN-γ was 0.47% on the average. The present inventors defined cutting value as 1%, which was obtained by doubling the average value (0.47%) considering a standard deviation. That is, when the ratio of IFN-γ+ cells to CD8+ cells was 1% or more, response was considered to be positive.

Figure 2:
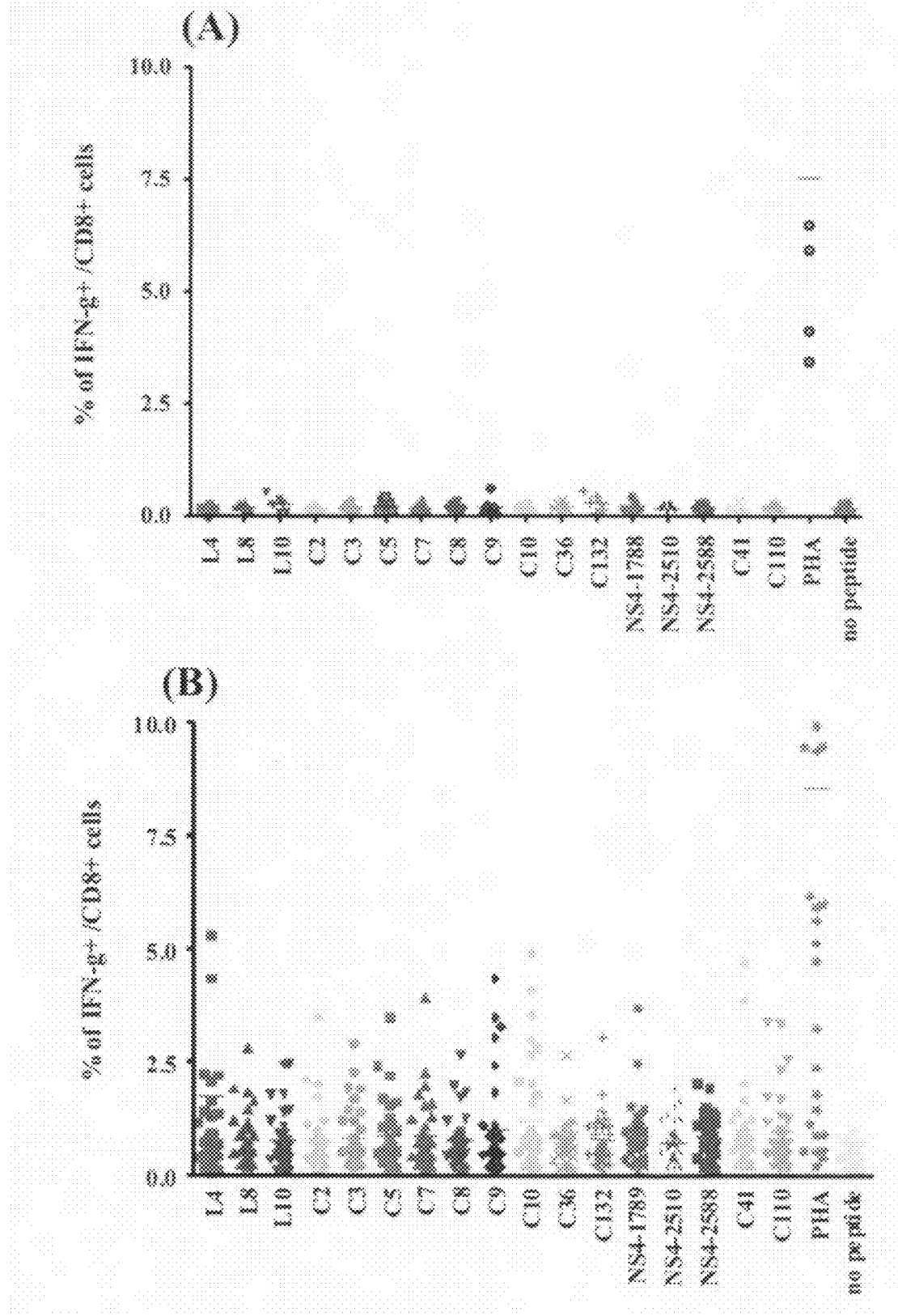
FIG. 2: a view illustrating the increased secretion level of cytokine IFN-γ in HCV-infected patients, which was determined by in vitro ICS assay after administering the epitopes of the present invention for 5 days.
(A): Normal subject group
(B): HCV patients group

As shown in FIG. 2, the 10 inventive epitopes effectively activated memory T cells in HCV-infected patients.

Example 5

Construction of Expression Vectors

Figure 3:
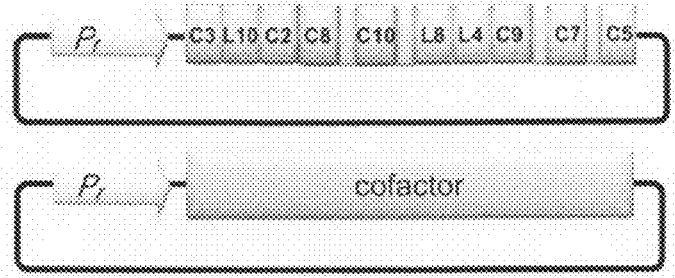
FIG. 3: a schematic diagram illustrating the epitope expression vector and the cofactor expression vector constructed in Example 5.
(A): schematic diagram of epitope-encoding DNA and cofactor-encoding DNA
(B): schematic diagram illustrating human chimeric IL-15-encoding DNA
Figure 3:
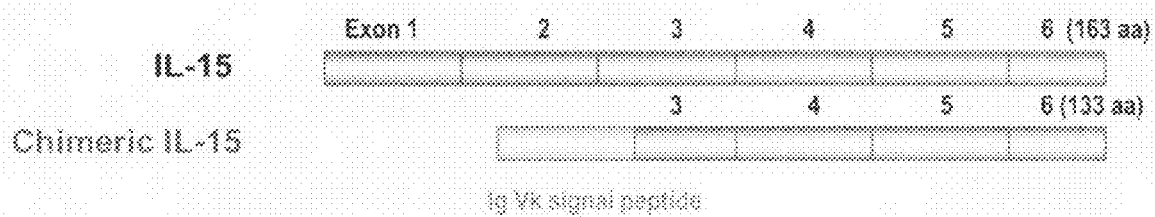

In this Example, expression vectors expressing an epitope and a cofactor, respectively, were constructed as shown in FIG. 3.

<5-1> Construction of Epitope Expression Vectors

The order of the arrangement of the 10 epitopes obtained in Example 3 was determined using proteasome (ParProc: paproc2.de/paproc1/paproc1.html) and TAP tools (TAPPred, imtech.res.in/raghava/tappred/). Based on the determined antigen sequences, codon optimization for the 10 epitopes was performed using a graphical codon usage analyser (web site: gcua.schoedl.de/) in order to induce an effective epitope expression in mammalian cells, and the results are shown in FIG. 4. Then, a polynucleotide encoding the epitopes was synthesized by PTDS (PCR-based Two-step DNA synthesis).

In detail, 10 primers as set forth in SEQ ID NOS: 33 to 42 were first synthesized based on PTDS (Ai-Sheng Xiong et al., *Nucleic Acids Research*, 32, e98 (2004)). Then, the primer of SEQ ID NO: 33 and the primer of SEQ ID NO: 42 (40 pmole each) were mixed with 1 pmole of each of the 8 remaining primers of SEQ ID NOS: 34 to 41, and MgSO₄ (2 mM), dNTP (0.2 mM each), 10×PCR buffer (1×) and 2 U of platinum Taq polymerase (Gibco-BRL) were mixed. Then, PCR was performed as follows: predenaturation at 94° C. for 2 minutes; 29 cycles (denaturation at 94° C. for 15 seconds, annealing at 50° C. for 30 seconds, polymerization at 68° C. for 1 minute); and final extension at 68° C. for 5 minutes. The PCR products were stored at 4° C.

The second PCR was performed using 1 μl of the PCR products as a template and the primers of SEQ ID NOS: 33 and 42. In more detail, the primers of SEQ ID NOS: 33 and 42

(40 pmol each) were mixed with $MgSO_4$ (2 mM), dNTP (0.2 mM), and platinum Taq polymerase (2 U). PCR was performed as follows: predenaturation at 94° C. for 2 minutes; 24 cycles (denaturation at 94° C. for 15 seconds, annealing at 55° C. for 30 seconds, polymerization at 68° C. for 1 minute); and final extension at 68° C. for 5 minutes. The PCR products were stored at 4° C.

As a result of DNA sequencing, it was confirmed that the final PCR products had a nucleotide sequence as set forth in SEQ ID NO: 43. The sequence of SEQ ID NO: 43 included nucleotide sequences encoding preexisting epitopes, C18, $NS4_{1789}$ and $Core_{132}$, and these epitopes were used as control epitopes to evaluate epitope-specific CD8 T cell responsiveness. Although not distinctly shown, IgK signal sequence were added to 5' end, and flanking residues were inserted between epitope-encoding oligonucleotides, so that correct epitope production was stably carried out.

The PCR products were cloned into a pcDNA3.11V5-His TOPO expression vector (KS800-40, Invitrogen). Hereinafter, the expression vectors expressing these 13 epitopes are referred to simply as "M13 expression vectors."

Meanwhile, in order to construct expression vectors excluding the above three HLA-A2 control epitopes (C18, $NS4_{1789}$ and $Core_{132}$), first PCR was performed using the M13 expression vectors as a template and a set of primers of SEQ ID NOS: 66 and 67 under the following PCR condition: predenaturation at 94° C. for 2 minutes; 29 cycles (denaturation at 94° C. for 20 seconds, annealing at 55° C. for 30 seconds, polymerization at 68° C. for 1 minute); and final extension at 68° C. for 5 minutes, for the signal sequence, and a set of primer of SEQ ID NOS: 68 and 69 under the following PCR condition: predenaturation at 94° C. for 2 minutes; 29 cycles (denaturation at 94° C. for 20 seconds, annealing at 60° C. for 30 seconds, polymerization at 68° C. for 1 minute); and final extension at 68° C. for 5 minutes, for M10 epitope sequence.

Then, second PCR was performed using the first PCR products as a template and the primers of SEQ ID NOS: 66 and 69 under the following PCR condition: predenaturation at 94° C. for 2 minutes; 29 cycles (denaturation at 94° C. for 20 seconds, annealing at 55° C. for 30 seconds, polymerization at 68° C. for 1 minute); and final extension at 68° C. for 5 minutes.

The PCR products were cloned into a pcDNA3.1/V5-His TOPO expression vector (KS800-40, Invitrogen). As a result of DNA sequencing, it was confirmed that the final PCR products had a nucleotide sequence as set forth in SEQ ID NO: 70. Hereinafter, the expression vectors expressing these 10 epitopes are referred to simply as "M10 expression vectors."

<5-2> Construction of Cofactor Expression Vectors

In those chronic hepatitis patients, CTL-mediated immune response is too weak to kill a virus causing chronic viral infection, and the expressions of cofactors known to promote cell-mediated immune response are very low, which leads to the immaturity of dendritic cells known as APCs. Also, the number of natural killer cells is low and the function of the cells is suppressed. Thus, many attempts have been made to enhance CTL-mediated immunity by transfecting cells with a cofactor-encoding gene.

Thus, in the Example, cofactor expression vectors were constructed by inserting genes encoding cofactors (or co-stimulatory molecules), FLT-3L, 4-1BBL, IL-15, CD80 and CD40LT (a trimer form of CD40L) into pcDNA3.1/V5-His TOPO expression vectors (Invitrogen). For this, RNA for each of FLT-3L, 4-1BBL, IL-15, CD80 and CD40L was extracted from mouse dendritic cells, and splenocytes, and RT-PCR was then performed to obtain cDNA.

In more detail, in order to construct vectors expressing FLT-3L, 4-1BBL, IL-15 or CD80, as shown in Table 7 below, 40 pmole of each of forward and reverse primers, 2 µg of cDNA, 2 µl of 50 mM $MgSO_4$ (final conc. 2 mM), 1 µl of 10 mM dNTP (0.2 mM each), 0.4 µl of 5 U/µl platinum Taq polymerase (2 U) and distilled water were mixed to make a final volume of 50 µl. PCR was performed as follows: predenaturation at 94° C. for 2 minutes; 29 cycles (denaturation at 94° C. for 15 seconds, annealing for 30 seconds, polymerization at 68° C. for 1 minute); and final extension at 68° C. for 5 minutes. The PCR products were stored at 4° C.

TABLE 7

| Cofactor | | Primer sequence | Annealing temperature |
|---|---|---|---|
| FLT3L | Forward | SEQ ID NO: 44 | 55° C. |
| | Reverse | SEQ ID NO: 45 | |
| 4-1BBL | Forward | SEQ ID NO: 46 | 50° C. |
| | Reverse | SEQ ID NO: 47 | |
| IL-15 | Forward | SEQ ID NO: 48 | 50° C. |
| | Reverse | SEQ ID NO: 49 | |
| CD80 | Forward | SEQ ID NO: 50 | 55° C. |
| | Reverse | SEQ ID NO: 51 | |

CD40LT was cloned by the following four consecutive PCR rounds. In detail, first PCR was performed using cDNA of CD40L as a template and primers as set forth in SEQ ID NOS: 57 and 58. The first PCR products were cloned into a pcDNA3.1/V5-His TOPO expression vector (Invitrogen). Then, second PCR was performed using the expression vector as a template and primers as set forth in SEQ ID NOS: 56 and 57 to clone a nucleotide sequence encoding amino acids 111 to 260 corresponding to an extracellular domain. Then, third PCR was performed using the second PCR products as a template and primers as set forth in SEQ ID NOS: 52 to 55 to obtain a CD40L trimer (CD40LT) having an IL-7 leader sequence and a leucine zipper motif. Then, forth PCR was performed using the third PCR products as a template and primers as set forth in SEQ ID NOS: 52 and 57 to combine the second PCR products and the third PCR products. The above PCRs were performed in the same manner as described above except the concentrations of primers and annealing temperatures.

The final PCR products were cloned into a pcDNA3.1/V5-His TOPO expression vector (Invitrogen). DNA sequencing demonstrated that the final PCR products were cloned into the pcDNA3.1/V5-His TOPO expression vector. The primers used for the above PCR are summarized in Table 8 below.

TABLE 8

| PCR | | Primer sequence | Primer Concentration (pmole) | Annealing temperature (° C.) |
|---|---|---|---|---|
| First PCR | Forward | SEQ ID NO: 58 | 50 | 55° C. |
| | Reverse | SEQ ID NO: 57 | 50 | |
| Second PCR | Forward | SEQ ID NO: 56 | 20 | 60° C. |
| | Reverse | SEQ ID NO: 57 | 20 | |
| Third PCR | $1^{st}$ Forward | SEQ ID NO: 52 | 40 | 60° C. |
| | $1^{st}$ Reverse | SEQ ID NO: 53 | 1 | |
| | $2^{nd}$ Forward | SEQ ID NO: 54 | 1 | |
| | $2^{nd}$ Reverse | SEQ ID NO: 55 | 40 | |
| Fourth PCR | Forward | SEQ ID NO: 52 | 20 | 60° C. |
| | Reverse | SEQ ID NO: 57 | 20 | |

Human IL-15 gene was cloned into the same vector according to the reference (*Eur. J. Immunol.* 27: 1049-1054 (1997),

*Eur. J. Immunol.* 29: 1265-1274 (1997)) to construct chimeric human IL-15-encoding vectors. As shown in (B) of FIG. 3, the chimeric human IL-15-encoding DNA is deleted exon 1, exon 2, and partial exon 3 from IL-15-encoding DNA, and has the Ig VK signal peptide in N-terminus. As a result of DNA sequencing, it was confirmed that the final PCR products had a nucleotide sequence as set forth in SEQ ID NO: 71.

Example 6

Selection of Immune Stimulatory Factors that Induce T Cell-Mediated Immune Response Against the Inventive Epitopes in DNA-Immunized Mouse Model DNA immunization was performed in HLA-A2.1 transgenic mice in order to determine whether or not CTL-mediated immune response was increased when cofactors were introduced together with the inventive epitopes.

The M13 expression vector of Example <5-1> and the cofactor expression vector of Example <5-2> (50:50, v/v (%)) were resuspended in PBS to a concentration of 1 μg/μl. 10 uM/100 μl of cardiotoxin was injected into the tibialis anterior of mice (Charles River, Japan) (8 weeks old). Two days later, 100 μg of the resultant DNA mixture of the epitope expression vector and the cofactor expression vector was injected into the same areas. Seven days later, boosting was performed with the same amount of DNA. 14 days after the DNA boosting, splenocytes were isolated from the mice, put in each well of a 12-well plate to a concentration of $1 \times 10^7$ cells/well and cultured a R-10 medium (RPMI 1640 medium containing 10% FCS, 2 mM L-glutamine, 50 U/ml penicillin and 50 μg/ml streptomycin). 10 μg/ml of the epitope peptides encoded in M13 expression vector were added to each well. Three days later, 10 ng/ml of recombinant mouse IL-2 (calbiochem, German) was added thereto. Five days later, the cells were collected, resuspended in the RPMI-10 medium to a concentration of $1 \times 10^5$ cells/100 ul, and loaded into each well of a 96-well plate coated with anti-mouse IFN-γ antibody. The mouse splenocytes were irradiated with 3000 rad and pulsed with 10 μg/ml of the epitope peptides at 37° C. for 1 hour.

$3 \times 10^5$ the resultant cells were loaded into each well of multiscreen plate (Millipore, MAHA S45 10). ELISPOT assay was performed as described in Example 3. At that time, the antibody used for coating the well was rat anti-mouse IFN-γ antibody (BD Pharmingen, CA). Biotinylated rat anti-mouse IFN-γ antibody (BD pharmingen, CA) and strptavidin-HRPO (BD Pharmingen, CA) were additionally used.

Figure 5:
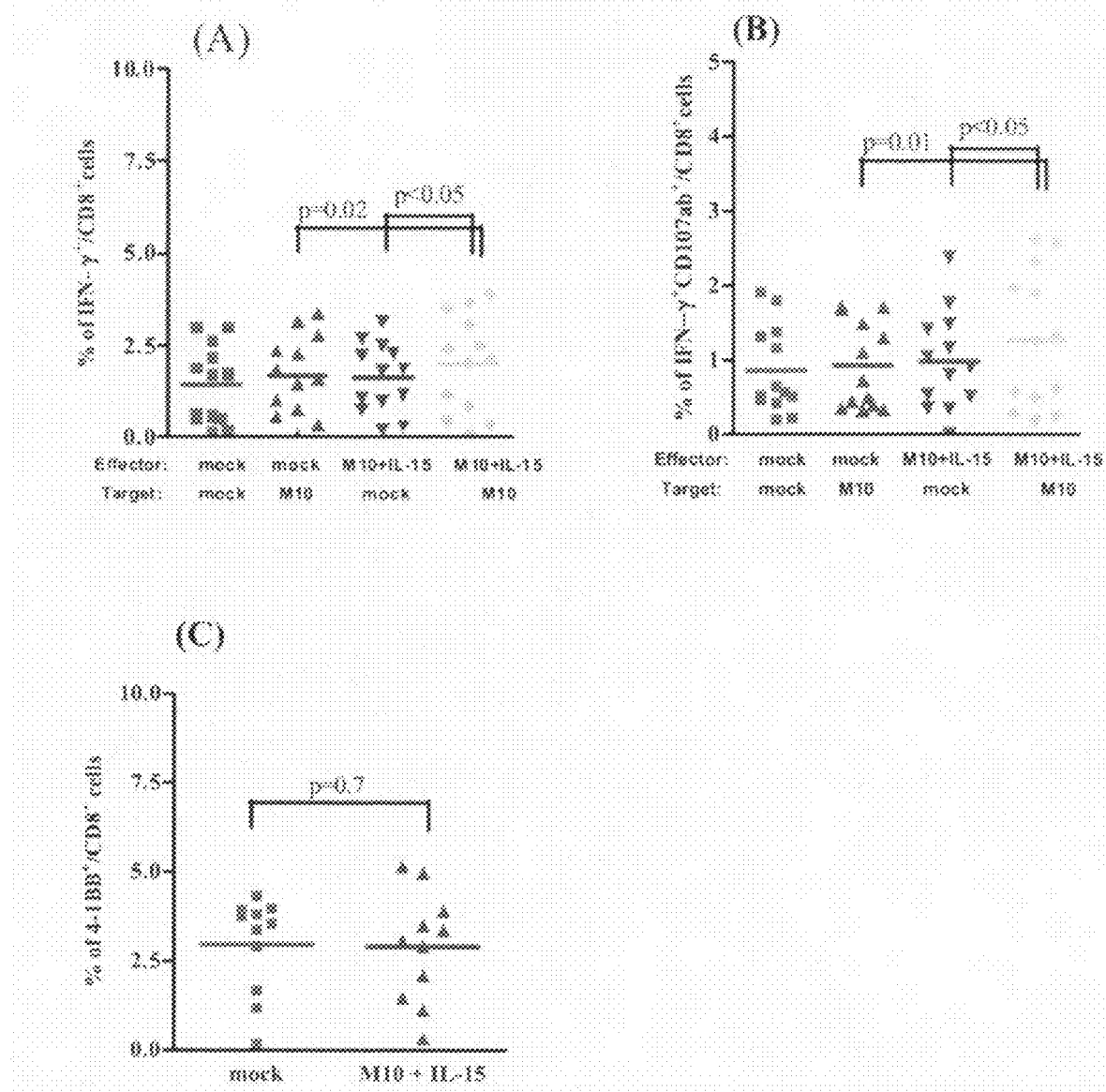
FIG. 5: a graph illustrating the increased secretion level of cytokine IFN-γ in HLA-A2.1-transfected mice, which was determined by in vitro ICS assay after co-administration of the mice with the epitope expression vector and the cofactor expression vector of Example 5.

As shown in FIG. 5, CTL-mediated immune response was much greater when cofactors were injected together with an epitope-encoding DNA than when only an epitope-encoding DNA was injected. In particular, co-administration of the epitopes with CD40LT, IL-15, 4-1BBL, or CD80 resulted in higher increase of immune response.

Example 7

Analysis of T Cell-Mediated Immune Response by Stimulation with Dendritic Cells Derived from HCV-Infected Patients Expressing the Invented Epitopes by DNA Transfection To evaluate the capacity of the M10 DNA construct in inducing epitope-specific CTL responses, patients' lymphocytes were stimulated with M10-transfected dendritic cells before vaccination into animal model.

Antigen-presenting cells (APC) play an important role in recognition of a foreign antigen by T cells in vivo. B cells, macrophages, and dendritic cells can function as APCs. In particular, dendritic cells are known as representative APCs.

In the Example, mature dendritic cells were produced in vitro. Prior to the experiments, the M10 expression vectors obtained in Example <5-1> were amplified in *E. coli* and purified using an endotoxin free kit (Qiagene). The $A_{260}/A_{280}$ ratio of the epitope expression vectors was measured using a spectrophotometer (Biochrom). The $A_{260}/A_{280}$ ratio was 1.6 or more, which means that the epitope expression vectors were highly purified. 1 μg/μl of the epitope expression vectors were used for the experiments.

In order to obtain mature dendritic cells, CD14+ monocytes were isolated from the PBMCs obtained in Example <2-1> using magnetic beads. The separated monocytes were loaded into each well of a 6-well plate at a density of $1 \times 10^6$ cells/well. Recombinant human IL-4 (1000 U/ml) and recombinant human GM-CSF (1000 U/ml) were added thereto, and the cells were cultured at 37° C. for 8 days. At day 3, 50% of the cell culture was replaced with RPMI-10 supplemented with cytokines (recombinant human IL-4 (1000 U/ml) and human GM-CSF (1000 U/ml)). At day 6, a monocyte-conditioned medium (*Blood.* 90(9):3640-3646 (1997), *J Exp Med.* 178(3):1067-1076 (1993)) and cytokines (recombinant human IL-4 (1000 U/ml) and human GM-CSF (1000 U/ml)) were added to induce the maturation of dendritic cells. At day 8, the cells were collected and phenotypes (CD14$^-$, CD80$^+$, CD86$^+$, CD83$^+$, CD1a$^+$, Class I$^{high}$, Class II$^{high}$) of the mature dendritic cells were determined.

$1 \times 10^6$ dendritic cells were transfected with 4 μg of the M10 expression vectors using an electroporator (Nucleofector™, Amaxa). To calculate the expression level and survival after DNA transfection, GFP-encoding plasmid DNA was transfected into dendritic cells in the same manner as above. GFP-expressing cells were counted, and it was found that 60% or more of the cells was expressed.

Dendritic cells transfected with the above epitope expression vectors were mixed with the PBMCs obtained in Example 2 at the ratio of 1:10, and then cultured at 37° C. Five days later, the cells were collected and T cell immunity was measured by ELISPOT assay. Once DNA is expressed in cytoplasm in the form of a polypeptide, it is cut into epitope peptides by TAP, and APCs recognize each epitope peptide. Accordingly, the measurement of SFCs for each epitope peptide cut by TAP was performed according to ELISPOT assay.

Figure 6:
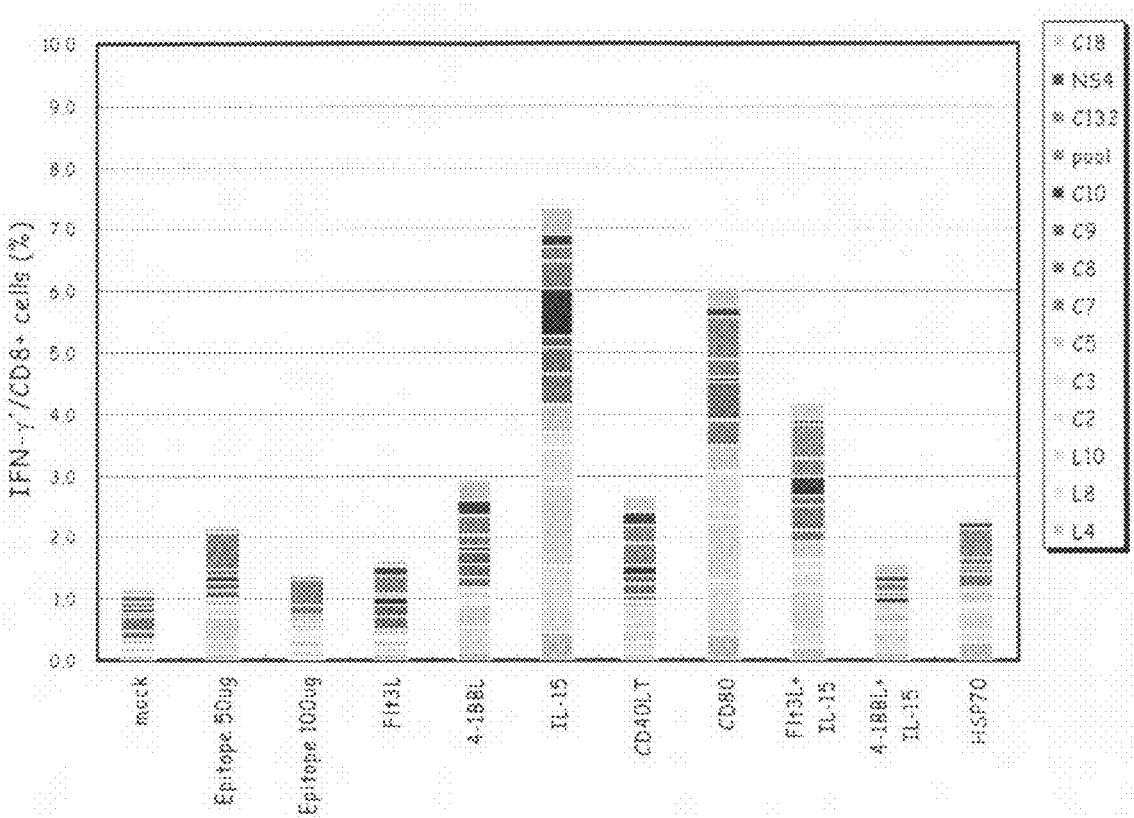
FIG. 6: a graph illustrating the increased secretion level of cytokine IFN-γ in HCV-infected patient' T cells, which was determined by in vitro ICS assay after transfecting the epitope expression vector of Example 5 into dendritic cells separated from blood samples of the patients.
(A): Immunogenicity of epitope
(B): Cytotoxicity of CTL
(C): Activity of T cell

The results are shown in FIG. 6. In FIG. 6, mock DNA means a pcDNA3.1 vector. As shown in FIG. 6, the inventive epitope expression vectors exhibited an effective cellular immunity in HCV-infected cells.

Example 8

Evaluation of the Efficacy for Epitope-Based DNA Vaccine in HCV-Infected Chimpanzee Model Naked DNA vaccines were immunized into three chronically HCV-infected chimpanzees (*Pan Troglodytes*) having the characteristics summarized in Table 9 below without any adjuvant like cardiotoxin, unlike in Example 6. The M10 expression vectors were used as an antigen, and IL-15 was used as a cofactor. The chimpanzees were housed at the New Iberia Research Center (NIRC) with approval for the experiment from the University of Lafayette-NIRC Animal Care and Use Committee. The chimpanzees were handled in accordance with NIRC standards.

TABLE 9

| Chimpanzee | Age (yrs) | Weight (kg) | Initial viral load (IU/ml) | HCV genotype | Sex |
|---|---|---|---|---|---|
| Chimp 1 | 10 | 54 | 23,100 | 1a | M |
| Chimp 2 | 9 | 49 | 5,090 | 1a | M |
| Chimp 3 | 26 | 65 | 7,790 | 1a | M |

10 mg of the DNA mixture of the epitope expression vector and the human chimeric IL-15 expression vector of Example 5 in 5 ml of PBS was administered to three sites of gluteus maximus and two sites of deltoid muscles (1 ml/site). Three administrations were performed at week 0, 4 and 8. The chimpanzee test took six months.

In order to evaluate the inventive epitope-specific cellular immunity, ex vivo IFN-γ ELISPOT assay was conducted in Chimp 1, 2 and 3. The results are shown in (A) and (B) of FIG. 7.

Figure 7:
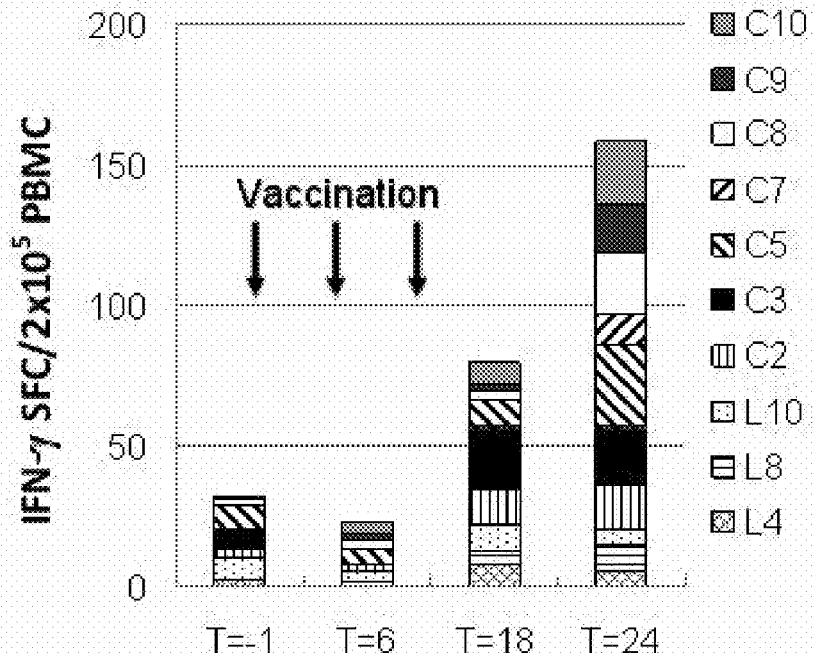
FIG. 7: graphs illustrating the increased secretion levels of cytokine IFN-γ in two HCV-infected chimpanzees, Chimp 1 and 2, respectively, which were determined by ex vivo ELISPOT assay after co-injection of the chimpanzees with the epitope expression vector and the IL-15 expression vector of Example 5.
(A): ex vivo IFN-γ secretion against the invented epitopes in Chimp 1
(B): ex vivo IFN-γ secretion against the invented epitopes in Chimp 2
(C): ex vivo IFN-γ secretion against pre-existing epitopes in Chimp 1
Figure 7B:
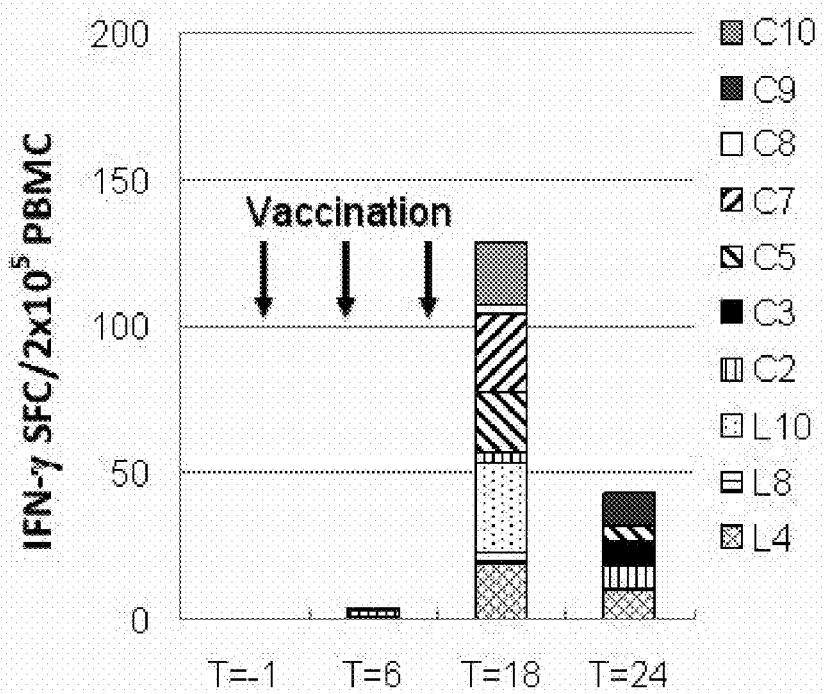
Figure 7C:
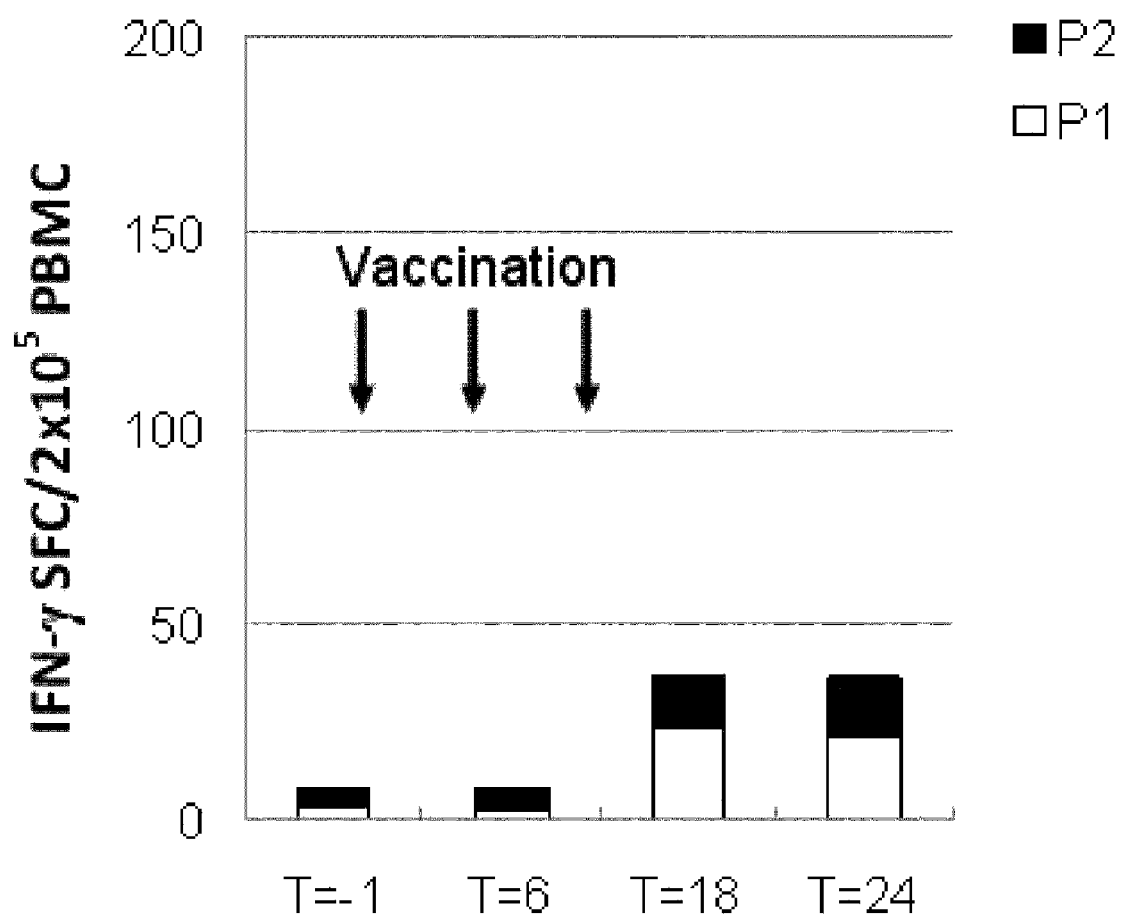

As shown in (A) and (B) of FIG. 7, the administration of the inventive epitopes into Chimp 1 and 2 significantly increased IFN-γ levels, thus improving cellular immunity. This vaccination with epitope DNA and IL-15 DNA also increased specific T cell responses to pre-existing epitopes P1 and P2 (corresponding to $NS5a_{2267}$ and $NS5a_{2273}$ in reference, *Nature Medicine* (2006)12:190) in Chimp 1 (see (C) of FIG. 7)

Figure 8A:
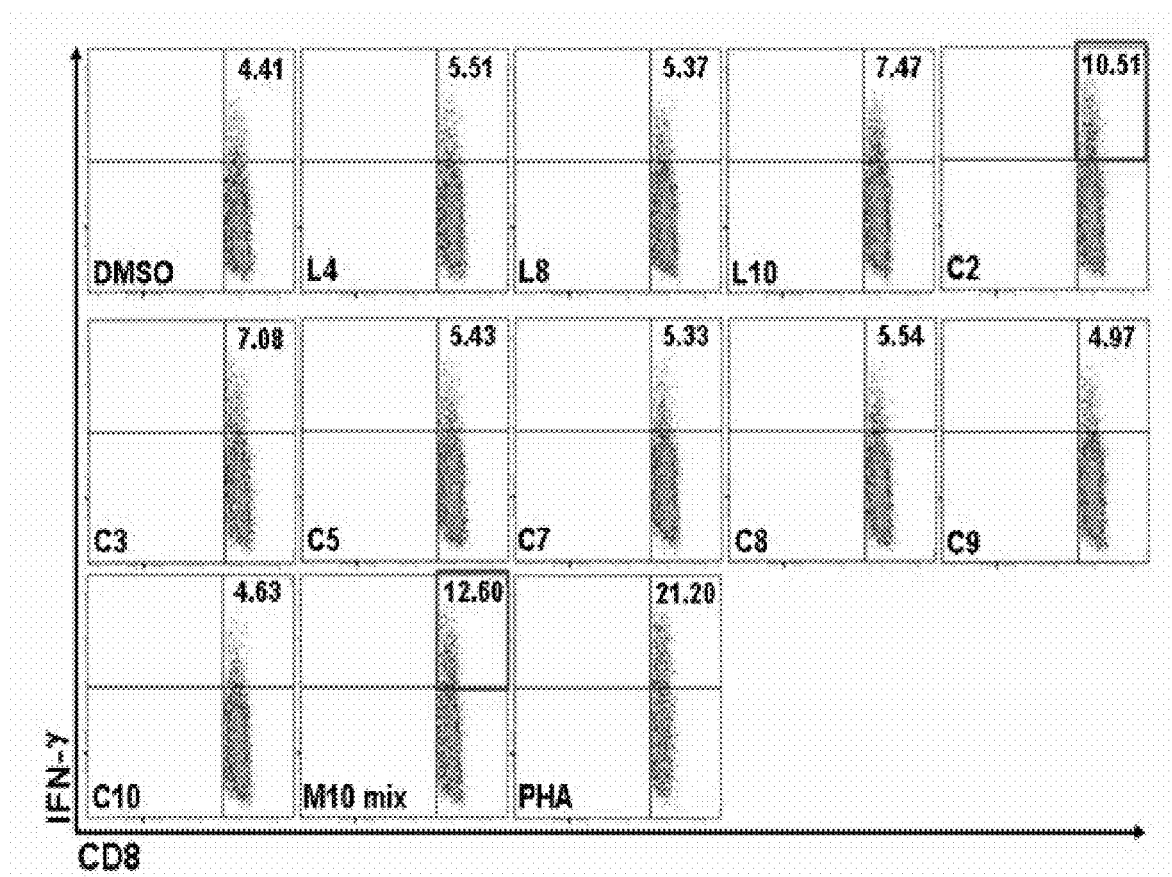
FIG. 8: gating scheme for identification of IFN-γ+ CD8 T-cells for HCV-infected chimpanzees, Chimp 1 and Chimp 3 after in vitro stimulation with epitopes for 21 days.
Figure 8B:
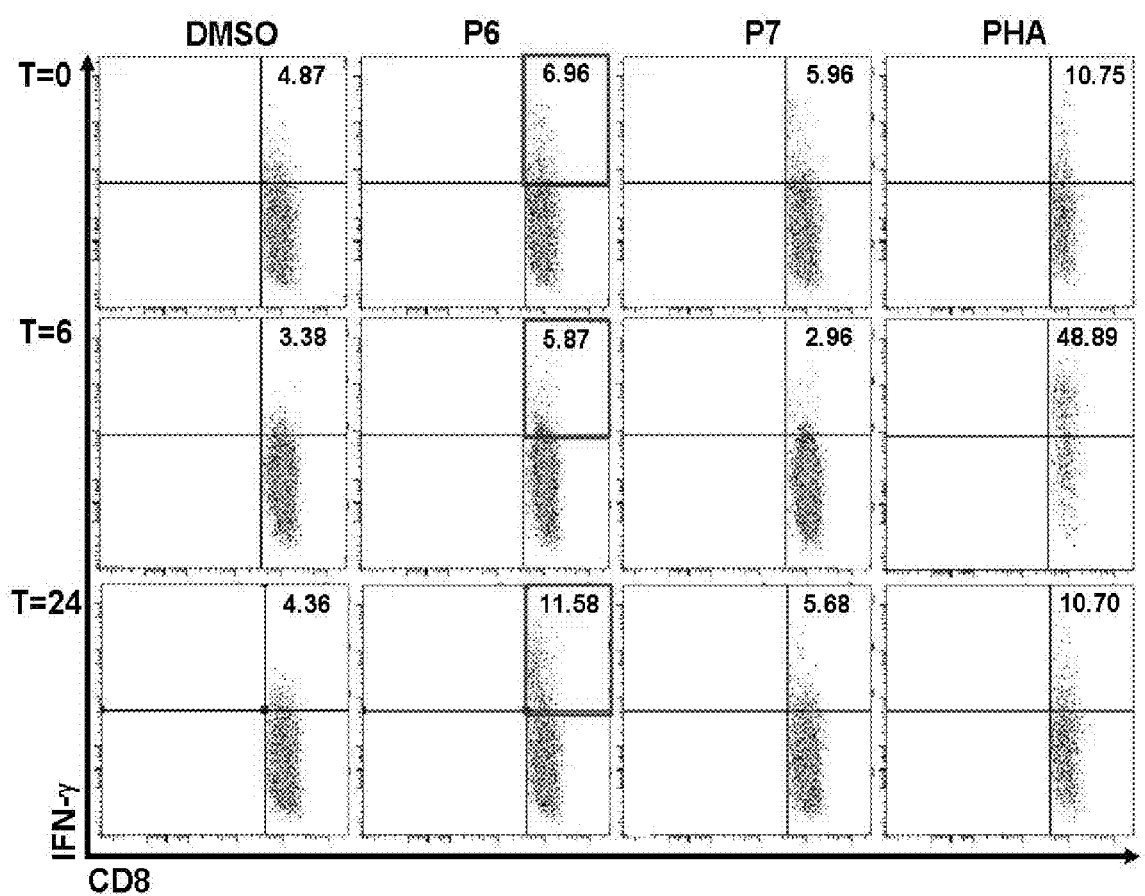

Meanwhile, the ex vivo ELISPOT analysis result obtained for Chimp 3 did not show a significantly increased secretion of IFN-γ. However, Chimp 3 showed a significant increase of IFN-γ+ CD8+ T-cells after expansion for 21 days followed by in vitro stimulation with individual or mixture of invented epitope peptides. PBMCs collected at week 24 showed a significant increase of IFN-γ+ CD8+ T-cells (see FIG. 8 A) upon stimulation with C2 and M10 epitopes. This result shows that the memory CTL responses can be recruited by stimulation with epitope in a vaccinated animal even though activated CTL is not detected ex vivo.

Ex vivo ELISPOT analysis showed that Chimp 3 didn't exhibit epitope specific T cell responses not only to the inventive epitopes but also to pre-existing epitopes P6 and P7 (corresponding to $Core_{130}$ and $NS5a_{2251}$ in reference, *Science*, 302:659 (2003)). However, by in vitro stimulation with the pre-existing epitopes for 21 days followed by in vitro stimulation, a significant increase of IFN-γ+ CD8+ T-cells was detected by ICS analysis (see FIG. 8 B), showing that the vaccination of invented epitope coding DNA and IL-15 DNA can elicit memory T cell responses.

The above results demonstrate that the inventive epitopes can effectively induce an HCV-specific cellular immunity in vivo.

While the invention has been described with respect to the above specific embodiments, it should be recognized that various modifications and changes may be made and also fall within the scope of the invention as defined by the claims that follow.

What is claimed is:

1. An isolated polynucleotide molecule, encoding a polypeptide consisting of HCV epitopes, and include the sequences of SEQ ID NOs: 1, 3, 5, 7, 9, 11, 13, 15, 17, and 19.

2. The isolated polynucleotide molecule of claim 1, further comprising at least one of the sequences selected from the group consisting of SEQ ID NOs: 21, 23, 25, 27, 29, and 31.

3. An immunogenic composition comprising the isolated polynucleotide of claim 2.

4. An eukaryotic expression vector comprising the isolated polynucleotide of claim 1.

5. An immunogenic composition comprising the isolated polynucleotide of claim 1.

6. An immunogenic composition comprising the eukaryotic expression vector of claim 4.

7. The immunogenic composition of claim 5, further comprising a cofactor selected from the group consisting of CD4OLT, 4-1BBL, IL-15, FLT-3L, B7-1, B7-2, and a heat shock protein.

8. The immunogenic composition of claim 5, further comprising a mature dendritic cell.

9. A method of inducing an anti-HCV immune response to HLA-A and HLA-B types, comprising administering the polynucleotide of claim 1 to a subject.

10. A method of inducing an anti-HCV immune response to HLA-A and HLA-B types, comprising administering the eukaryotic expression vector of claim 4 to a subject.

11. The method of claim 9, further comprising administering to the subject a cofactor selected from the group consisting of CD4OLT, 4-1BBL, IL-15; FLT-3L, B7-1, B7-2, and a heat shock protein.

12. The method of claim 9, further comprising administering a mature dendritic cell.

13. An immunogenic composition comprising isolated polynucleotide molecules encoding peptides consisting of HCV epitopes, including:

the isolated polynucleotide of SEQ ID NO: 7;
the isolated polynucleotide of SEQ ID NO: 1;
the isolated polynucleotide of SEQ ID NO: 3;
the isolated polynucleotide of SEQ ID NO: 5;
the isolated polynucleotide of SEQ ID NO: 9;
the isolated polynucleotide of SEQ ID NO: 11;
the isolated polynucleotide of SEQ ID NO: 13;
the isolated polynucleotide of SEQ ID NO: 15;
the isolated polynucleotide of SEQ ID NO: 17; and
the isolated polynucleotide of SEQ ID NO: 19.

14. The immunogenic composition of claim 13, further comprising at least of:

the isolated polynucleotide of SEQ ID NO: 21;
the isolated polynucleotide of SEQ ID NO: 23;
the isolated polynucleotide of SEQ ID NO: 25;
the isolated polynucleotide of SEQ ID NO: 27;
the isolated polynucleotide of SEQ ID NO: 29; and
the isolated polynucleotide of SEQ ID NO: 31.

15. The immunogenic composition of claim 13, further comprising a cofactor selected from the group consisting of CD4OLT, 4-1BBL, IL-15, FLT-3L, B7-1, B7-2, and a heat shock protein.

* * * * *

SEQUENCE LISTING

```
<160> NUMBER OF SEQ ID NOS: 81

<210> SEQ ID NO 1
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 1 tac gcc gcc cag ggc tac aag gtg ctg                          27
Tyr Ala Ala Gln Gly Tyr Lys Val Leu
  1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Tyr Ala Ala Gln Gly Tyr Lys Val Leu
  1               5

<210> SEQ ID NO 3
<211> LENGTH: 27
<212> TYPE: DNA
<213> ORGANISM: Artificial Sequence
<220> FEATURE:
<223> OTHER INFORMATION: Synthetic construct
<220> FEATURE:
```

-continued

```
<221> NAME/KEY: CDS
<222> LOCATION: (1)..(27)

<400> SEQUENCE: 3 gcc ctg ccc ccc agg gcc tac gcc atg                          27
Ala Leu Pro Pro Arg Ala Tyr Ala Met
 1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Ala Leu Pro Pro Arg Ala Tyr Ala Met
 1               5

<210> SEQ ID NO 5
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 5 ctg ctg ctg gcc atc ctg ggc ccc ctg                          27
Leu Leu Leu Ala Ile Leu Gly Pro Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Leu Leu Leu Ala Ile Leu Gly Pro Leu
 1               5

<210> SEQ ID NO 7
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 7 aag tgc gac gag ctg gcc gcc aag ctg                          27
Lys Cys Asp Glu Leu Ala Ala Lys Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8
```

```
Lys Cys Asp Glu Leu Ala Ala Lys Leu
  1               5
```

<210> SEQ ID NO 9
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 9

```
gcc cag ggc tac aag gtg ctg gtg ctg                          27
Ala Gln Gly Tyr Lys Val Leu Val Leu
  1               5
```

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

```
Ala Gln Gly Tyr Lys Val Leu Val Leu
  1               5
```

<210> SEQ ID NO 11
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 11

```
acc atc ctg ggc atc ggc acc gtg ctg                          27
Thr Ile Leu Gly Ile Gly Thr Val Leu
  1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic construct

<400> SEQUENCE: 12

```
Thr Ile Leu Gly Ile Gly Thr Val Leu
  1               5
```

<210> SEQ ID NO 13
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 13

```
tac gtg cag atg gcc ctg atg aag ctg                          27
Tyr Val Gln Met Ala Leu Met Lys Leu
  1               5
```

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Tyr Val Gln Met Ala Leu Met Lys Leu
 1               5

<210> SEQ ID NO 15
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 15 atg gcc ctg atg aag ctg gcc gcc ctg                         27
Met Ala Leu Met Lys Leu Ala Ala Leu
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Met Ala Leu Met Lys Leu Ala Ala Leu
 1               5

<210> SEQ ID NO 17
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 17 gcc gcc tcc tgc ggc ggc gcc gtg ttc                         27
Ala Ala Ser Cys Gly Gly Ala Val Phe
 1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Ala Ala Ser Cys Gly Gly Ala Val Phe
 1               5

<210> SEQ ID NO 19
<211> LENGTH: 27
<212> TYPE: DNA
<213> ORGANISM: Artificial Sequence

```
<220> FEATURE:
<223> OTHER INFORMATION: Synthetic construct
<220> FEATURE:
<221> NAME/KEY: CDS
<222> LOCATION: (1)..(27)

<400> SEQUENCE: 19 ttc gtg ggc ctg gcc ctg ctg acc ctg                          27
Phe Val Gly Leu Ala Leu Leu Thr Leu
 1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Phe Val Gly Leu Ala Leu Leu Thr Leu
 1               5

<210> SEQ ID NO 21
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 21 aac ctg ggc aag gtg atc gac acc ctg                          27
Asn Leu Gly Lys Val Ile Asp Thr Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Asn Leu Gly Lys Val Ile Asp Thr Leu
 1               5

<210> SEQ ID NO 23
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 23 tac gtg ggc ggc gtg gag cac agg ctg                          27
Tyr Val Gly Gly Val Glu His Arg Leu
 1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 24

Tyr Val Gly Gly Val Glu His Arg Leu
  1               5

<210> SEQ ID NO 25
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 25 aag gtg agg atg tac gtg ggc ggc gtg                              27
Lys Val Arg Met Tyr Val Gly Gly Val
  1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic construct

<400> SEQUENCE: 26

Lys Val Arg Met Tyr Val Gly Gly Val
  1               5

<210> SEQ ID NO 27
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 27 gag ctg atc ttc gac atc acc aag ctg                              27
Glu Leu Ile Phe Asp Ile Thr Lys Leu
  1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Glu Leu Ile Phe Asp Ile Thr Lys Leu
  1               5

<210> SEQ ID NO 29
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 29
```

```
acc gcc ggc gcc agg ctg gtg gtg ctg                          27
Thr Ala Gly Ala Arg Leu Val Val Leu
 1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic construct

<400> SEQUENCE: 30

Thr Ala Gly Ala Arg Leu Val Val Leu
 1               5

<210> SEQ ID NO 31
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(27)

<400> SEQUENCE: 31 gcc atc ctg ggc ccc ctg atg gtg ttc                          27
Ala Ile Leu Gly Pro Leu Met Val Phe
 1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic construct

<400> SEQUENCE: 32

Ala Ile Leu Gly Pro Leu Met Val Phe
 1               5

<210> SEQ ID NO 33
<211> LENGTH: 62
<212> TYPE: DNA
<213> ORGANISM: Artificial Sequence
<220> FEATURE:
<223> OTHER INFORMATION: Synthetic construct

<400> SEQUENCE: 33
gtttaaacgc cgccaccatg ggaatgcagg tgcagatcca gagcctgttt ctgctcctcc   60
tg                                                                 62

<210> SEQ ID NO 34
<211> LENGTH: 59
<212> TYPE: DNA
<213> ORGANISM: Artificial Sequence
<220> FEATURE:
<223> OTHER INFORMATION: Synthetic construct

<400> SEQUENCE: 34
gggcaggaag gcggcctttc ctctggaccc gggcacccac aggaggagca gaaacaggc    59

<210> SEQ ID NO 35
<211> LENGTH: 77
<212> TYPE: DNA
<213> ORGANISM: Artificial Sequence
<220> FEATURE:
```

<223> OTHER INFORMATION: Synthetic construct

<400> SEQUENCE: 35
gaaaggccgc cttcctgccc tccgacttct tccccagcgt gaaggcccag ggctacaagg    60
tgctggtgct gaagctg    77

<210> SEQ ID NO 36
<211> LENGTH: 77
<212> TYPE: DNA
<213> ORGANISM: Artificial Sequence
<220> FEATURE:
<223> OTHER INFORMATION: Synthetic construct

<400> SEQUENCE: 36
cagcttggcg gccagctcgt cgcacttggc gttcaggggg cccaggatgg ccagcagcag    60
cttcagcacc agcacct    77

<210> SEQ ID NO 37
<211> LENGTH: 77
<212> TYPE: DNA
<213> ORGANISM: Artificial Sequence
<220> FEATURE:
<223> OTHER INFORMATION: Synthetic construct

<400> SEQUENCE: 37
acgagctggc cgccaagctg aacatggccc tgatgaagct ggccgccctg aacttcgtgg    60
gcctggccct gctgacc    77

<210> SEQ ID NO 38
<211> LENGTH: 80
<212> TYPE: DNA
<213> ORGANISM: Artificial Sequence
<220> FEATURE:
<223> OTHER INFORMATION: Synthetic construct

<400> SEQUENCE: 38
caccttgtag ccctgggcgg cgtagttcat ggcgtaggcc ctgggggca gggccttcag    60 ggtcagcagg gccaggccca    80

<210> SEQ ID NO 39
<211> LENGTH: 77
<212> TYPE: DNA
<213> ORGANISM: Artificial Sequence
<220> FEATURE:
<223> OTHER INFORMATION: Synthetic construct

<400> SEQUENCE: 39
ccgcccaggg ctacaaggtg ctgaacgccg cctcctgcgg cggcgccgtg ttcaaggccg    60
cctacgtgca gatggcc    77

<210> SEQ ID NO 40
<211> LENGTH: 77
<212> TYPE: DNA
<213> ORGANISM: Artificial Sequence
<220> FEATURE:
<223> OTHER INFORMATION: Synthetic construct

<400> SEQUENCE: 40
cagggaggcc ttcagcacgg tgccgatgcc caggatggtg gccttcagct tcatcagggc    60
catctgcacg taggcgg    77

<210> SEQ ID NO 41
<211> LENGTH: 89
<212> TYPE: DNA
<213> ORGANISM: Artificial Sequence
<220> FEATURE:
<223> OTHER INFORMATION: Synthetic construct

<400> SEQUENCE: 41
accgtgctga aggcctccct gatggccttc accgccgccg tgaaggacct gatgggctac        60 atcccctgg tgacgcgttg agtttaaac                                           89

<210> SEQ ID NO 42
<211> LENGTH: 23
<212> TYPE: DNA
<213> ORGANISM: Artificial Sequence
<220> FEATURE:
<223> OTHER INFORMATION: Synthetic construct

<400> SEQUENCE: 42
gtttaaactc aacgcgtcac cag                                                23

<210> SEQ ID NO 43
<211> LENGTH: 514
<212> TYPE: DNA
<213> ORGANISM: Artificial Sequence
<220> FEATURE:
<223> OTHER INFORMATION: Synthetic construct

<400> SEQUENCE: 43
gtttaaacgc cgccaccatg ggaatgcagg tgcagatcca gagcctgttt ctgctcctcc        60
tgtgggtgcc cggtccaga ggaaaggccg ccttcctgcc ctccgacttc ttccccagcg       120
tgaaggccca gggctacaag gtgctggtgc tgaagctgct gctggccatc ctgggccccc       180
tgaacgccaa gtgcgacgag ctggccgcca agctgaacat ggccctgatg aagctggccg       240
ccctgaactt cgtgggcctg gccctgctga ccctgaaggc cctgccccc agggcctacg       300 ccatgaacta cgccgcccag ggctacaagg tgctgaacgc cgcctcctgc ggcggcgccg       360
tgttcaaggc cgcctacgtg cagatggccc tgatgaagct gaaggccacc atcctgggca       420
tcggcaccgt gctgaaggcc tccctgatgg ccttcaccgc cgccgtgaag gacctgatgg       480
gctacatccc cctggtgacg cgttgagttt aaac                                  514

<210> SEQ ID NO 44
<211> LENGTH: 46
<212> TYPE: DNA
<213> ORGANISM: Artificial Sequence
<220> FEATURE:
<223> OTHER INFORMATION: Synthetic construct

<400> SEQUENCE: 44
gagtttaaac gccgccacca tgacagtgct ggcgccagcc tggagc                       46

<210> SEQ ID NO 45
<211> LENGTH: 39
<212> TYPE: DNA
<213> ORGANISM: Artificial Sequence
<220> FEATURE:
<223> OTHER INFORMATION: Synthetic construct

<400> SEQUENCE: 45
tcgtttaaac ttacctgggc cgaggctctg ggagctccg                               39

<210> SEQ ID NO 46

```
<211> LENGTH: 47
<212> TYPE: DNA
<213> ORGANISM: Artificial Sequence
<220> FEATURE:
<223> OTHER INFORMATION: Synthetic construct

<400> SEQUENCE: 46
gagtttaaac gccgccacca tggaccagca cacacttgat gtggagg          47

<210> SEQ ID NO 47
<211> LENGTH: 38
<212> TYPE: DNA
<213> ORGANISM: Artificial Sequence
<220> FEATURE:
<223> OTHER INFORMATION: Synthetic construct

<400> SEQUENCE: 47
tcgtttaaac tcattcccat gggttgtcgg gtttcaca                    38

<210> SEQ ID NO 48
<211> LENGTH: 50
<212> TYPE: DNA
<213> ORGANISM: Artificial Sequence
<220> FEATURE:
<223> OTHER INFORMATION: Synthetic construct

<400> SEQUENCE: 48
gagtttaaac gccgccacca tgaaaatttt gaaaccatat atgaggaata       50

<210> SEQ ID NO 49
<211> LENGTH: 39
<212> TYPE: DNA
<213> ORGANISM: Artificial Sequence
<220> FEATURE:
<223> OTHER INFORMATION: Synthetic construct

<400> SEQUENCE: 49
tcgtttaaac tcaggacgtg ttgatgaaca tttggacaa                   39

<210> SEQ ID NO 50
<211> LENGTH: 47
<212> TYPE: DNA
<213> ORGANISM: Artificial Sequence
<220> FEATURE:
<223> OTHER INFORMATION: Synthetic construct

<400> SEQUENCE: 50
gagtttaaac gccgccacca tggcttgcaa ttgtcagttg atgcagg          47

<210> SEQ ID NO 51
<211> LENGTH: 39
<212> TYPE: DNA
<213> ORGANISM: Artificial Sequence
<220> FEATURE:
<223> OTHER INFORMATION: Synthetic construct

<400> SEQUENCE: 51
tcgtttaaac ctaaaggaag acggtctgtt cagctaatg                   39

<210> SEQ ID NO 52
<211> LENGTH: 65
<212> TYPE: DNA
<213> ORGANISM: Artificial Sequence
<220> FEATURE:
<223> OTHER INFORMATION: Synthetic construct

<400> SEQUENCE: 52
```

```
gagtttaaac gccgccacca tgttccatgt ttctttaga tatatctttg gaattcctcc    60
actga                                                               65

<210> SEQ ID NO 53
<211> LENGTH: 70
<212> TYPE: DNA
<213> ORGANISM: Artificial Sequence
<220> FEATURE:
<223> OTHER INFORMATION: Synthetic construct

<400> SEQUENCE: 53
gtcgctgctg gtagatgatg tgacaggcag cagaacaagg atcagtggag gaattccaaa    60
gatatatcta                                                           70

<210> SEQ ID NO 54
<211> LENGTH: 69
<212> TYPE: DNA
<213> ORGANISM: Artificial Sequence
<220> FEATURE:
<223> OTHER INFORMATION: Synthetic construct

<400> SEQUENCE: 54
gtcacatcat ctaccagcag cgacaggatg aagcagatcg aggacaagat cgaggagatc    60
ctgagcaag                                                            69

<210> SEQ ID NO 55
<211> LENGTH: 72
<212> TYPE: DNA
<213> ORGANISM: Artificial Sequence
<220> FEATURE:
<223> OTHER INFORMATION: Synthetic construct

<400> SEQUENCE: 55
gccgatcagc ttcttgatcc tggcgatctc gttctcgatg tggtagatct tgctcaggat    60
ctcctcgatc tt                                                        72

<210> SEQ ID NO 56
<211> LENGTH: 66
<212> TYPE: DNA
<213> ORGANISM: Artificial Sequence
<220> FEATURE:
<223> OTHER INFORMATION: Synthetic construct

<400> SEQUENCE: 56
gccaggatca agaagctgat cggcgagagg ctgctggaaa tgcaaagagg tgatgaggat    60
cctcaa                                                               66

<210> SEQ ID NO 57
<211> LENGTH: 43
<212> TYPE: DNA
<213> ORGANISM: Artificial Sequence
<220> FEATURE:
<223> OTHER INFORMATION: Synthetic construct

<400> SEQUENCE: 57
tcgtttaaac ctagagtttg agtaagccaa aagatgagaa gcc                      43

<210> SEQ ID NO 58
<211> LENGTH: 46
<212> TYPE: DNA
<213> ORGANISM: Artificial Sequence
<220> FEATURE:
```

<223> OTHER INFORMATION: Synthetic construct

<400> SEQUENCE: 58
gagtttaaac gccgccacca tgatagaaac atacagccaa ccttcc      46

<210> SEQ ID NO 59
<211> LENGTH: 9
<212> TYPE: PRT
<213> ORGANISM: Artificial Sequence
<220> FEATURE:
<223> OTHER INFORMATION: Synthetic construct

<400> SEQUENCE: 59

Leu Leu Pro Pro Arg Gly Pro Arg Leu
 1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic construct

<400> SEQUENCE: 60

Asp Leu Met Gly Tyr Ile Pro Leu Val
 1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic construct

<400> SEQUENCE: 61

Ser Leu Met Ala Phe Thr Ala Ala Val
 1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic construct

<400> SEQUENCE: 62

Ser Leu Thr Pro Pro His Ser Ala Lys
 1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic construct

<400> SEQUENCE: 63

Arg Val Cys Glu Lys Met Ala Leu Tyr
 1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 64

Gly Pro Arg Leu Gly Val Arg Ala Thr
  1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic construct

<400> SEQUENCE: 65

Asp Pro Arg Arg Arg Ser Arg Asn Leu
  1               5

<210> SEQ ID NO 66
<211> LENGTH: 74
<212> TYPE: DNA
<213> ORGANISM: Artificial Sequence
<220> FEATURE:
<223> OTHER INFORMATION: Synthetic construct

<400> SEQUENCE: 66
gtttaaacgc cgccaccatg ggaatgcagg tgcagatcca gagcctgttt ctgctcctcc      60
tgtgggtgcc cggg                                                       74

<210> SEQ ID NO 67
<211> LENGTH: 63
<212> TYPE: DNA
<213> ORGANISM: Artificial Sequence
<220> FEATURE:
<223> OTHER INFORMATION: Synthetic construct

<400> SEQUENCE: 67
cttcagcacc agcaccttgt agccctgggc tcctctggac ccgggcaccc acaggaggag      60
cag                                                                   63

<210> SEQ ID NO 68
<211> LENGTH: 26
<212> TYPE: DNA
<213> ORGANISM: Artificial Sequence
<220> FEATURE:
<223> OTHER INFORMATION: Synthetic construct

<400> SEQUENCE: 68
gcccagggct acaaggtgct ggtgct                                          26

<210> SEQ ID NO 69
<211> LENGTH: 27
<212> TYPE: DNA
<213> ORGANISM: Artificial Sequence
<220> FEATURE:
<223> OTHER INFORMATION: Synthetic construct

<400> SEQUENCE: 69
gtttaaactc acttcagcac ggtgccg                                         27

<210> SEQ ID NO 70
<211> LENGTH: 406
<212> TYPE: DNA
<213> ORGANISM: Artificial Sequence
<220> FEATURE:
<223> OTHER INFORMATION: Synthetic construct

<400> SEQUENCE: 70
```

```
gtttaaacgc cgccaccatg ggaatgcagg tgcagatcca gagcctgttt ctgctcctcc      60
tgtgggtgcc cgggtccaga ggagcccagg gctacaaggt gctggtgctg aagctgctgc     120
tggccatcct gggcccctg aacgccaagt gcgacgagct ggccgccaag ctgaacatgg      180
ccctgatgaa gctggccgcc ctgaacttcg tgggcctggc cctgctgacc ctgaaggccc     240
tgccccccag ggcctacgcc atgaactacg ccgcccaggg ctacaaggtg ctgaacgccg     300
cctcctgcgg cggcgccgtg ttcaaggccg cctacgtgca gatggccctg atgaagctga     360
aggccaccat cctgggcatc ggcaccgtgc tgaagtgagt ttaaac                    406

<210> SEQ ID NO 71
<211> LENGTH: 440
<212> TYPE: DNA
<213> ORGANISM: Artificial Sequence
<220> FEATURE:
<223> OTHER INFORMATION: Synthetic construct

<400> SEQUENCE: 71
gagtttaaac gccgccacca tggacttcca ggtgcagatc ttcagcttcc tgctgatcag      60
cgccagcgtg atcatgagcc gggccaactg ggtgaatgta ataagtgatt tgaaaaaaat     120
tgaagatctt attcaatcta tgcatattga tgctacttta tatacggaaa gtgatgttca     180
ccccagttgc aaagtaacag caatgaagtg ctttctcttg gagttacaag ttatttcact     240
tgagtccgga gatgcaagta ttcatgatac agtagaaaat ctgatcatcc tagcaaacaa     300
cagtttgtct tctaatggga atgtaacaga atctggatgc aaagaatgtg aggaactgga     360
ggaaaaaaat attaaagaat ttttgcagag ttttgtacat attgtccaaa tgttcatcaa     420
cacttcttga gtttaaacga                                                 440

<210> SEQ ID NO 72
<211> LENGTH: 27
<212> TYPE: DNA
<213> ORGANISM: Artificial Sequence
<220> FEATURE:
<223> OTHER INFORMATION: Synthetic construct

<400> SEQUENCE: 72 tat gca gcc caa ggg tac aag gta ctc                                   27

<210> SEQ ID NO 73
<211> LENGTH: 27
<212> TYPE: DNA
<213> ORGANISM: Artificial Sequence
<220> FEATURE:
<223> OTHER INFORMATION: Synthetic construct

<400> SEQUENCE: 73 gcg tta cca caa cga gca tac gcc atg                                   27

<210> SEQ ID NO 74
<211> LENGTH: 27
<212> TYPE: DNA
<213> ORGANISM: Artificial Sequence
<220> FEATURE:
<223> OTHER INFORMATION: Synthetic construct

<400> SEQUENCE: 74 atc ttg ctc gcc ata ctc ggt ccg ctc                                   27

<210> SEQ ID NO 75
```

```
<211> LENGTH: 27
<212> TYPE: DNA
<213> ORGANISM: Artificial Sequence
<220> FEATURE:
<223> OTHER INFORMATION: Synthetic construct

<400> SEQUENCE: 75 aaa tgt gac gag ctc gct gca aag ttg                          27

<210> SEQ ID NO 76
<211> LENGTH: 27
<212> TYPE: DNA
<213> ORGANISM: Artificial Sequence
<220> FEATURE:
<223> OTHER INFORMATION: Synthetic construct

<400> SEQUENCE: 76 gcc caa ggg tac aag gta ctc gtc tta                          27

<210> SEQ ID NO 77
<211> LENGTH: 27
<212> TYPE: DNA
<213> ORGANISM: Artificial Sequence
<220> FEATURE:
<223> OTHER INFORMATION: Synthetic construct

<400> SEQUENCE: 77 tcc atc ctg ggc att ggc aca gtc ctg                          27

<210> SEQ ID NO 78
<211> LENGTH: 27
<212> TYPE: DNA
<213> ORGANISM: Artificial Sequence
<220> FEATURE:
<223> OTHER INFORMATION: Synthetic construct

<400> SEQUENCE: 78 tat gtc caa atg gtt ctc atg aag ctg                          27

<210> SEQ ID NO 79
<211> LENGTH: 27
<212> TYPE: DNA
<213> ORGANISM: Artificial Sequence
<220> FEATURE:
<223> OTHER INFORMATION: Synthetic construct

<400> SEQUENCE: 79 atg gtt ctc atg aag ctg gcc gca ctg                          27

<210> SEQ ID NO 80
<211> LENGTH: 27
<212> TYPE: DNA
<213> ORGANISM: Artificial Sequence
<220> FEATURE:
<223> OTHER INFORMATION: Synthetic construct

<400> SEQUENCE: 80 gct gca tcg tgc gga ggc gcg gtt ttc                          27

<210> SEQ ID NO 81
<211> LENGTH: 27
<212> TYPE: DNA
<213> ORGANISM: Artificial Sequence
<220> FEATURE:
<223> OTHER INFORMATION: Synthetic construct
```

-continued

<400> SEQUENCE: 81 ttc ata ggt ctg gta ctc ctg acc ttg 27